US012232936B2

(12) United States Patent
Qureshi et al.

(10) Patent No.: US 12,232,936 B2
(45) Date of Patent: Feb. 25, 2025

(54) TAMPON WITH APPLICATOR SUBSTANTIALLY FREE OF COMPONENTS DERIVED FROM PETROLEUM

(71) Applicant: The Procter & Gamble Company, Cincinnati, OH (US)

(72) Inventors: Khalid Qureshi, Mason, OH (US); Fang Liu, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 327 days.

(21) Appl. No.: 17/479,189

(22) Filed: Sep. 20, 2021

(65) Prior Publication Data

US 2023/0090472 A1 Mar. 23, 2023

(51) Int. Cl.
*A61F 13/20* (2006.01)
*A61F 13/15* (2006.01)
(Continued)

(52) U.S. Cl.
CPC .... *A61F 13/2071* (2013.01); *A61F 13/15764* (2013.01); *A61F 13/2097* (2013.01);
(Continued)

(58) Field of Classification Search
CPC ............ A61F 13/2071; A61F 13/15764; A61F 13/2097; A61F 13/266; A61F 13/34;
(Continued)

(56) References Cited

U.S. PATENT DOCUMENTS 4,650,459 A * 3/1987 Sheldon ................. A61F 13/26
604/15
5,693,009 A * 12/1997 Fox ......................... A61F 13/26
604/15
(Continued)

FOREIGN PATENT DOCUMENTS

EP 613672 A1 * 9/1994 ............. A61F 13/26
WO 2007078413 A1 7/2007

OTHER PUBLICATIONS

PCT Search Report and Written Opinion for PCT/US2022/076637 dated Jan. 5, 2023, 13 pages.

*Primary Examiner* — Guy K Townsend
*Assistant Examiner* — Gabriella E Burnette
(74) *Attorney, Agent, or Firm* — Sarah M. DeCristofaro

(57) ABSTRACT

A tampon product including an applicator with a hollow barrel portion and an ejection plunger within the barrel portion, is disclosed. One or both of the barrel portion and the ejection plunger may have a cylindrical form and be formed of a paper, and have a coating applied to the paper, wherein the coating is not predominately constituted by a material derived from petroleum. The coated paper barrel portion and/or ejection plunger may be manufactured to as to exhibit a static Relative Sliding Resistance Coefficient (CSR) no greater than 0.250 and/or a kinetic CSR no greater than 0.210, for purposes of smooth manufacturing. In combination or alternatively, the coated paper barrel portion and/or ejection plunger may be manufactured to as to exhibit a static Gripping Slip Resistance Coefficient (CGSR) no less than 0.190 and/or a kinetic CGSR no less than 0.170, for purposes of consumer satisfaction.

19 Claims, 10 Drawing Sheets

(51) Int. Cl.
*A61F 13/26* (2006.01)
*A61F 13/34* (2006.01)

(52) U.S. Cl.
CPC ............ *A61F 13/266* (2013.01); *A61F 13/34* (2013.01); *A61F 2013/15284* (2013.01)

(58) Field of Classification Search
CPC .......... A61F 2013/15284; A61F 13/206; A61F 13/2085; A61F 13/2091; D21H 27/002
See application file for complete search history.

(56) References Cited

U.S. PATENT DOCUMENTS

| | | | |
|---|---|---|---|
| 6,733,482 B1* | 5/2004 | Coles | A61F 13/82 977/841 |
| 7,887,525 B2* | 2/2011 | Gorham | A61F 13/26 604/15 |
| 2003/0028177 A1* | 2/2003 | Berg, Jr. | A61F 13/26 604/385.18 |
| 2003/0097106 A1 | 5/2003 | Hasse et al. | |
| 2003/0236161 A1* | 12/2003 | Fedyk | A61F 13/26 493/480 |
| 2010/0016780 A1* | 1/2010 | VanDenBogart | A61F 13/26 604/15 |
| 2010/0198133 A1 | 8/2010 | Dougherty, Jr. et al. | |
| 2015/0233058 A1* | 8/2015 | Neumann | D21H 17/28 162/175 |
| 2021/0045942 A1* | 2/2021 | Chan | A61F 13/53 |
| 2022/0047429 A1* | 2/2022 | Schuler | A61F 13/2097 |
| 2023/0090472 A1* | 3/2023 | Qureshi | A61F 13/2085 604/12 |

* cited by examiner

TAMPON WITH APPLICATOR SUBSTANTIALLY FREE OF COMPONENTS DERIVED FROM PETROLEUM

BACKGROUND

Consumer products or portions thereof that have components derived from petroleum (such as but not limited to plastics), are currently becoming subject to increased regulation by governments in a number of countries, and growing disfavor in some segments of the consumer market. Some reasons for this relate generally to sustainability and/or environmental concerns.

Women have used tampons for many years to manage menstrual discharge. Many women prefer tampons provided inside disposable applicators (rather than tampons configured to be inserted via a finger ("digitally") without use of an applicator). The typical tampon applicator is configured to house and protect the new tampon from deformation and/or contamination prior to use, and then to facilitate application of the tampon when its use is desired.

Currently, many tampon applicators or parts thereof are formed of thermoplastics such as polyethylene. The properties of thermoplastics and known associated forming/molding technologies enable a manufacturer to efficiently make an applicator having relatively sophisticated features, which may be provided for purposes of functionality, convenience, comfort during use, ergonomics and/or esthetic appeal, thereby making it attractive and convenient to consumers.

Other types of tampon applicators currently marketed are formed of paperboard or cardboard. While such applicators reduce reliance on and use of materials derived from petroleum as compared to plastic applicators, currently, they typically continue to include components derived from petroleum, such as binders, adhesives and coatings.

Accordingly, there remain opportunities for improvements in materials selections and designs for components of tampon applicators, in ways that reduce use of materials derived from petroleum, while providing applicators that effectively perform their intended function and include features that please consumers.

DESCRIPTION OF EXAMPLES

Definitions

Figure 1:
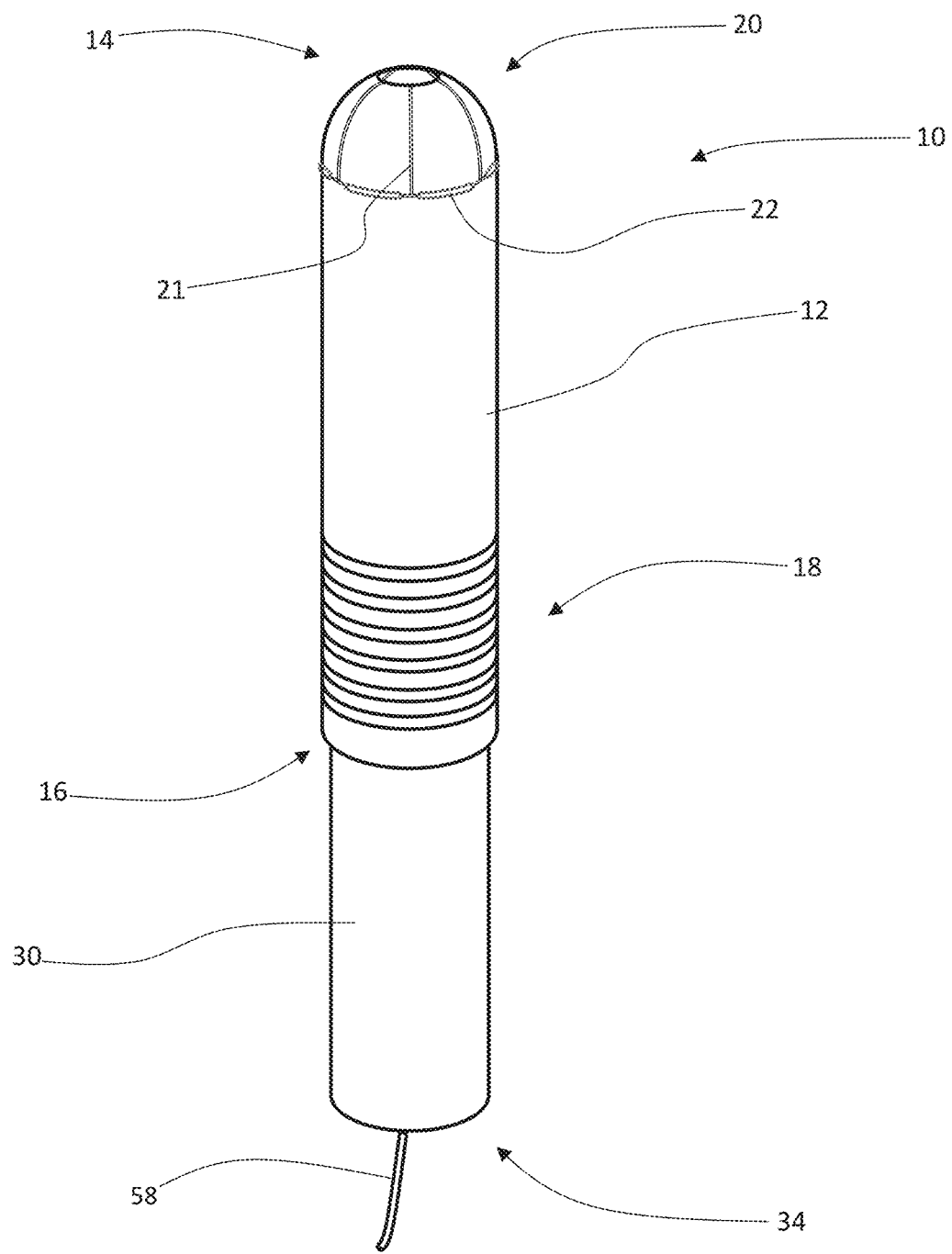
FIG. 1 is a perspective view of a tampon product with an applicator including a barrel portion and a plunger portion.

As used herein the term "tampon" refers to any type of absorbent structure which is configured to be inserted into the vaginal cavity for the interception and absorption of fluid therefrom. Typically, a tampon includes a pledget structure including a quantity of absorbent material, often absorbent fibrous material, which pledget structure has been bunched, folded and/or compressed in one or more lateral/radial directions, the longitudinal direction, or both, via application of pressure, heat and/or moisture control, in order to provide a formed tampon having a size, shape (typically approximately cylindrical) and stability of form to facilitate insertion into the vagina. A tampon which has been so formed is referred to herein has a "self-sustaining" form. The degree of compression, heat and moisture control applied to the pledget is sufficient such that in the subsequent absence of the external forces and absence of substantial contact with moisture, the pledget will tend to retain its general formed shape and size. It will be understood by persons of ordinary skill in the art that this self-sustaining form typically does not persist following insertion of the tampon. Once the tampon is inserted and begins to contact and absorb fluid, the pledget will swell with absorbed fluid and lose its self-sustaining form.

As used herein the terms "pledget" or "tampon pledget" are intended to be interchangeable and refer to a structure including absorbent material configured to perform the primary function of the tampon, absorption of menstrual fluid. A tampon pledget is sometimes referred to as a tampon blank, or a softwind, and the term "pledget" is intended to include structures designated by such terms as well.

As used herein "vaginal cavity" refers to the internal space within the genitalia of the human female, located between the introitus of the vagina (sometimes referred to as the sphincter of the vagina) and the cervix.

With respect to a tampon and an applicator, the "longitudinal" direction is the ordinary general direction of ejection from an applicator; and also corresponds with the ordinary general direction of insertion of a tampon and applicator into, and their withdrawal from, the vaginal cavity in normal use. For a completely manufactured, pre-use tampon that has a pledget with a generally cylindrical or capsule-shaped self-sustaining form, the longitudinal axis of the form lies generally or approximately along the longitudinal direction. A "radial" or "lateral" direction is a direction perpendicular to the longitudinal direction. The "lateral" direction is perpendicular to the longitudinal direction, and perpendicular to the z direction (defined below). Unless otherwise specified, references to "length" herein refer to a dimension along the longitudinal direction; references to "width" herein refer to a dimension along the lateral direction.

With respect to a tampon and an applicator, the term "forward" refers to a longitudinal direction of movement during normal insertion of the tampon and/or applicator by a user, and refers to portions of the tampon or applicator that lie closer to and/or enter the vaginal cavity earlier than other portions during normal insertion. Conversely, the term "rearward" refers to a longitudinal direction of movement during normal withdrawal of the tampon and/or applicator by a user, and refers to portions of the tampon or applicator that lie farther from and/or exit the vaginal cavity earlier than other portions during normal withdrawal.

A "nonwoven," "nonwoven web," "nonwoven web material," or "nonwoven fabric" is a cloth-like web material (or portion or section thereof) formed predominantly of fibers that are neither knitted nor woven, but rather, laid down and accumulated to a desired basis weight, then consolidated and held together to form a web, via one or any combination of calendering, thermal and/or compression bonding, bonding via use of a binder, heating (via, e.g., heated air driven through an accumulation of fibers) or hydroentangling (spunlace). The predominant fibers may be natural fibers harvested from plant material (e.g., cotton) (but excluding tree wood pulp), semi-synthetic (e.g., rayon, lyocell, viscose), or synthetic (e.g. fibers spun from molten thermoplastic polymer resin(s)), or any combination thereof. Herein, a skin- or membrane-like film (e.g., extruded or otherwise formed from polymer resin(s)) is not deemed a nonwoven. Herein, a paper tissue product, paper product, or paperboard or cardboard product, formed via wetlaying and predominantly constituted of tree wood pulp, is not deemed a nonwoven.

"Opened configuration," with respect to a tampon, means the configuration of the tampon prior to the time it is compressed and formed into a self-sustaining form during manufacture, or in the case of a finished product, after it is completely ejected from an applicator (if present) and/or allowed and/or caused by any suitable technique to open and substantially re-assume its pre-compression shape and size.

"Paper" means a material in web or sheet form, formed predominantly of cellulose fibers, for example, wood pulp fibers, which have been suspended in a slurry, which is then poured onto a moving mesh belt, drained of water, and subsequently dried over drying rollers, and in many examples, finished via calendering. In the resulting web or sheet product the cellulose fibers are interlaid and randomly oriented.

"Predominant," and forms thereof, when used to characterize a quantity of a constituent present in a composition, means that a majority of the weight of the material is constituted by the constituent.

"Withdrawal cord" refers to any section of string, yarn, cord, ribbon, strip material or other flexible/pliable elongate structure typically (although not necessarily) formed of fibrous material, attached to and/or extending from a tampon pledget and trailing from its rearward end. A withdrawal cord of sufficient length may be provided with a tampon for the purpose of providing a relatively thin and flexible trailing member of sufficient length to allow for a portion thereof to trail and remain outside of the introitus following full insertion of the tampon, which the user may easily grasp and pull to withdraw the tampon from her body following a desired duration of use.

With respect to a paper sheet or web product, when laid out flat on a horizontal planar surface, the "z direction" is a direction orthogonal to the horizontal planar surface, and is the direction along which caliper or thickness of the sheet or web (prior to rolling into paper tube product) would be measured.

Applicator Features

Figure 2A:
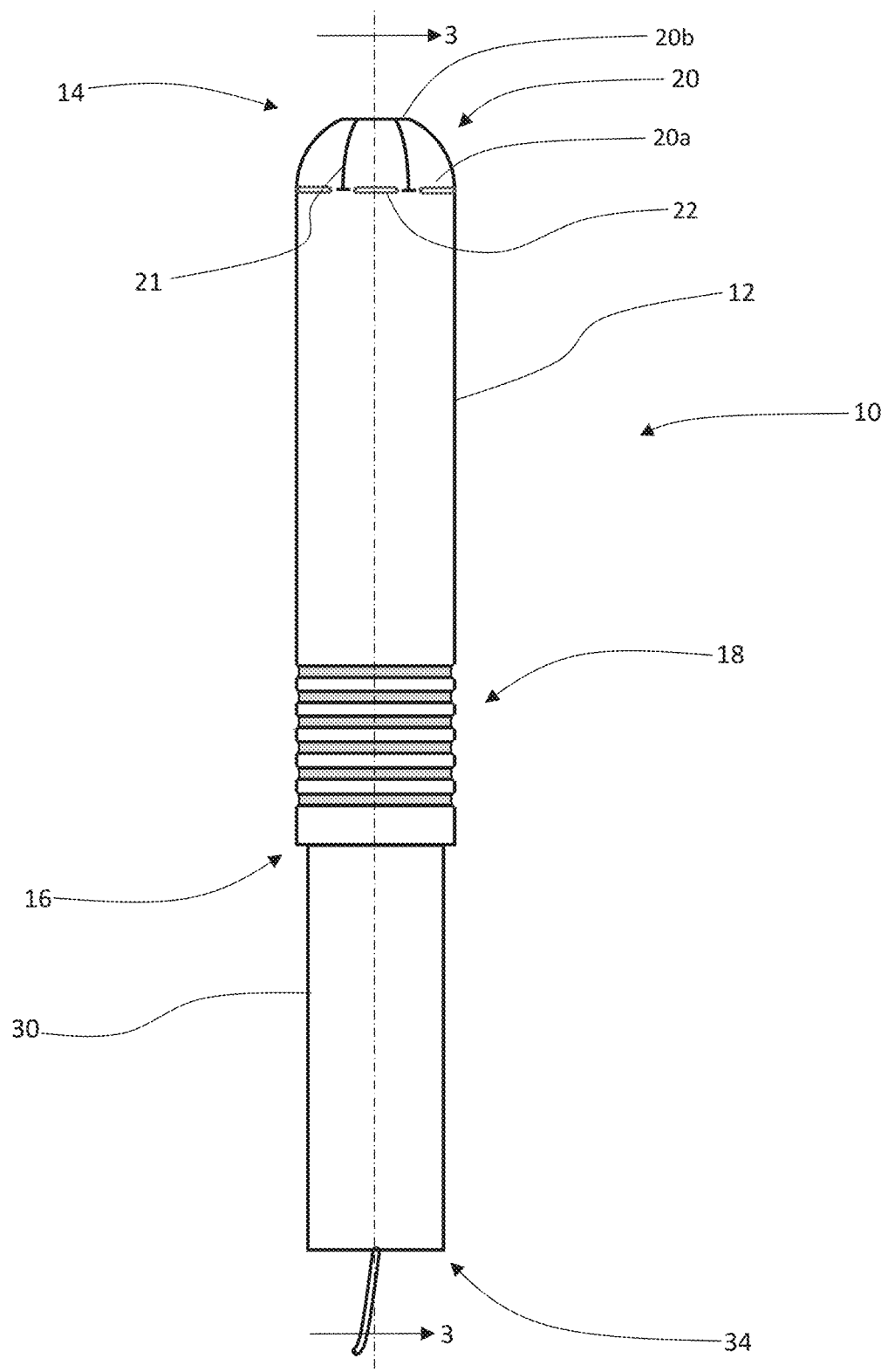
FIG. 2A is a longitudinal side view of the tampon product of FIG. 1.

Referring now to FIGS. 1-3, a tampon in a self-sustaining form, including a pledget 52 having a forward end 54 and rearward end 56, and a withdrawal cord 58 attached to the pledget and trailing from rearward end 56, may be supplied inside an applicator 10. Applicator 10 may be configured to house the tampon and protect it from contamination and/or unintended deformation prior to its use.

Applicator 10 may include a hollow barrel portion 12 and an ejection plunger 30, which also may be hollow. The barrel portion 12 and the ejection plunger 30 may be configured such that the ejection plunger 30 is at least partially disposed and longitudinally slidable within the barrel portion 12. In some examples including the examples illustrated in FIGS. 1-3, each of barrel portion 12 and ejection plunger 30 are hollow approximately cylindrical bodies, wherein the cylindrical form of ejection plunger 30 has an outer diameter that is smaller than an inner diameter of barrel portion 12, such that barrel portion 12 and ejection plunger 30 may be concentrically arranged and longitudinally slidable with respect to each other in telescope fashion.

Figure 2B:
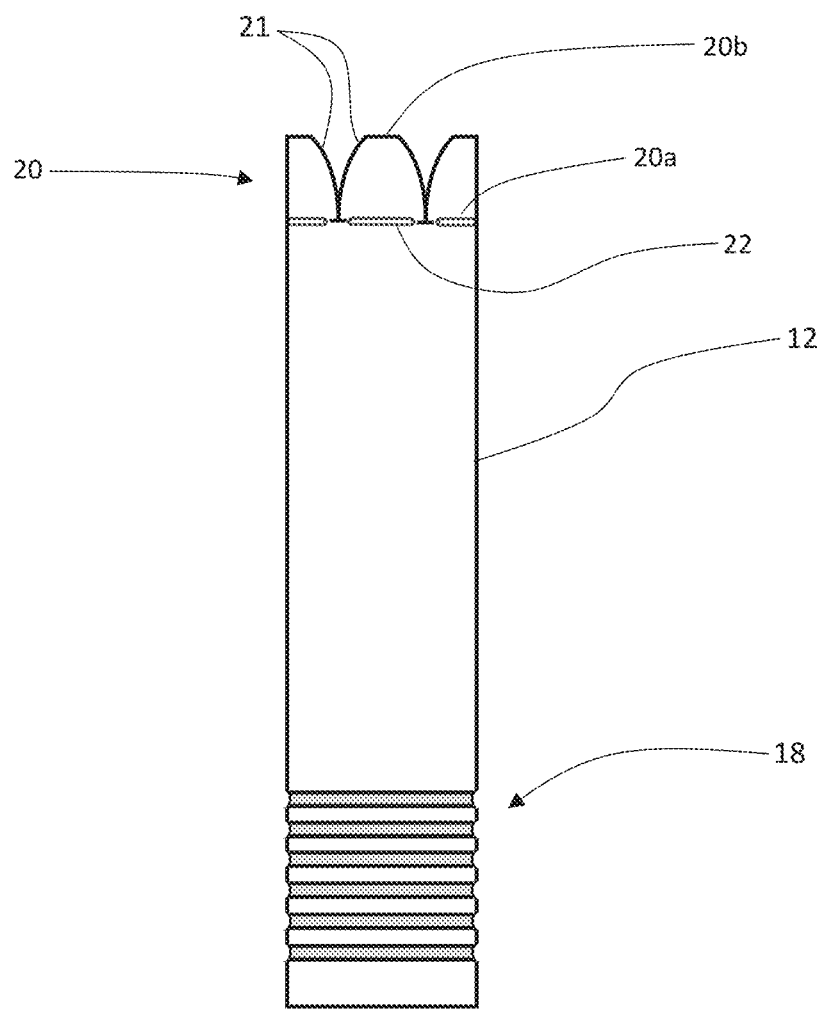
FIG. 2B is a longitudinal side view of a barrel portion of an applicator, prior to deformation of petals to their finished shapes and positions.

Barrel portion 12 may be provided with additional functional features. For example, forward end 14 of barrel portion 12 may include a plurality of petals 20 that have proximal bases 20a having outer surfaces coincident with the general cylindrical shape of the barrel portion 12, and distal ends 20b disposed radially inwardly of the proximal portions. The petals 20 and/or remainder of the barrel portion 12 may be configured such that the petals 20 may flex about the proximal bases 20a such that, upon forward longitudinal pressure exerted by the forward end 54 or pledget 52 during ejection via pressure form longitudinal forward movement of ejection plunger 30 relative barrel portion 12, the petals 20 will flex outwardly about their bases, thereby expanding an opening at forward end 14 of barrel portion 12, which allows the pledget to pass forwardly through the forward end 14 of the barrel portion 12, and out of the applicator. The petals 20 may be integrally formed with the remainder of the barrel portion 12. In some examples, the petals may be formed by making cuts 21 in a forward portion of a cylindrical precursor body of barrel portion 12 (for example, as shown in FIG. 2B), and then plastically deforming the remaining uncut portions radially inwardly, and with suitable curvature, to the positions depicted, by way of example, in FIGS. 1, 2A and 3. Such deformation may be accomplished in some examples via use of a forming die or mold (not shown), and may be facilitated in some examples via application of heat and/or steam. Additionally, in some examples the barrel portion 12 may be imparted with localized flexure zones 22 that demark the proximal bases 20a of the petals, which are zones about which the material of the barrel portion and/or petals more readily flexes or hinges, for example, as a result of a localized reduction in thickness or caliper of the material in flexure zones 22. Flexure zones 22 may be imparted by, e.g., molding or localized compression applied during the manufacturing process.

Barrel portion 12 may also be provided with gripping surface features 18 that enable the user to tactilely identify the rearward portion of barrel portion 12, and also enhance gripping slip resistance during use of the applicator. In a simple form as shown in the figures, gripping surface features 18 may be a series of circumferential grooves and/or ridges about the outer surface of the barrel portion 12 proximate its rearward end 16. More complex gripping surface features may be provided, however, of any design desired for purposes of functionality and esthetic appeal. Gripping surface features may be imparted to barrel portion 12 via forming techniques including molding, embossing, etc.

Figure 3A:
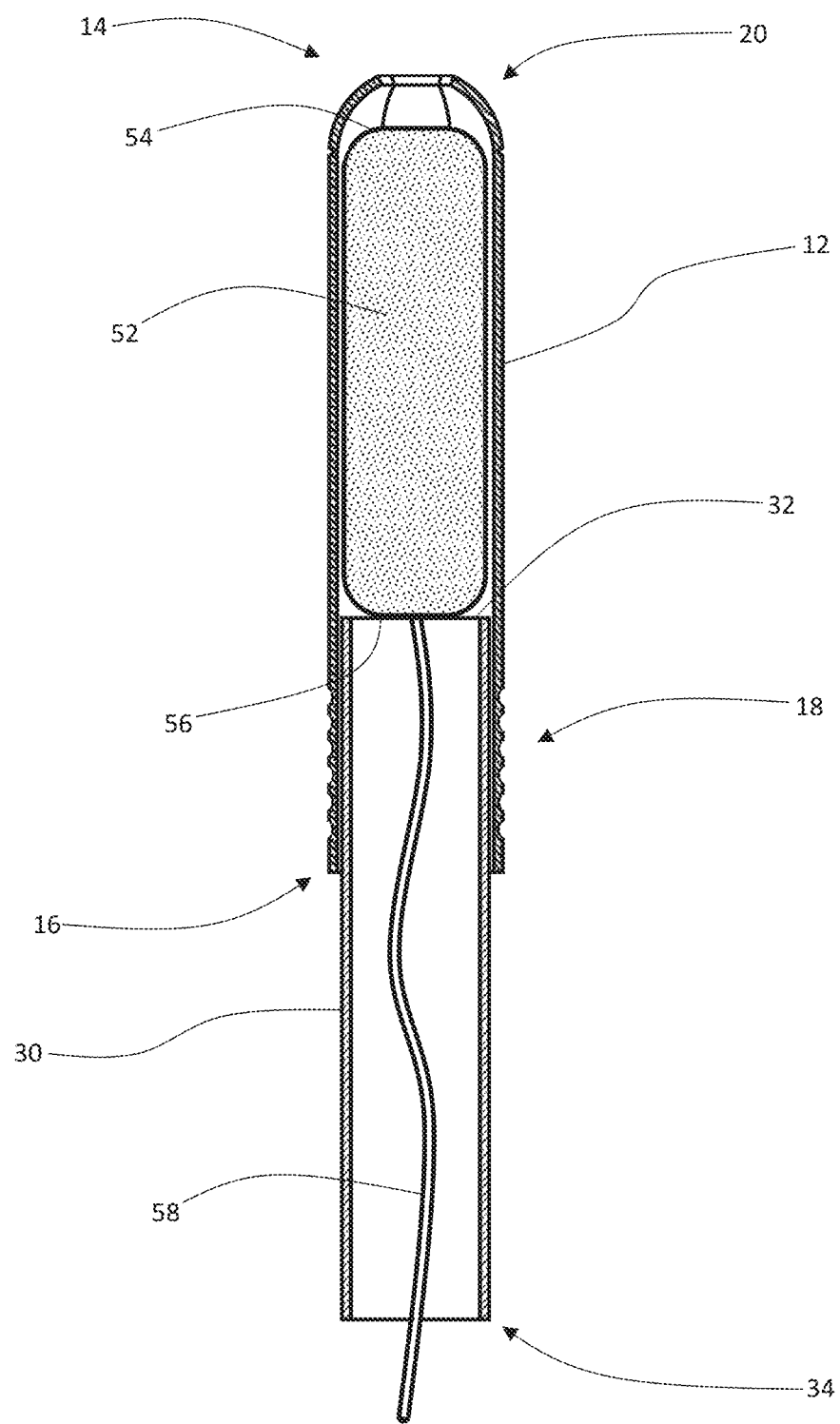
FIG. 3A is a longitudinal cross section of the tampon product of FIG. 3A, taken through line 3-3 identified in FIG. 2A.
Figure 3B:
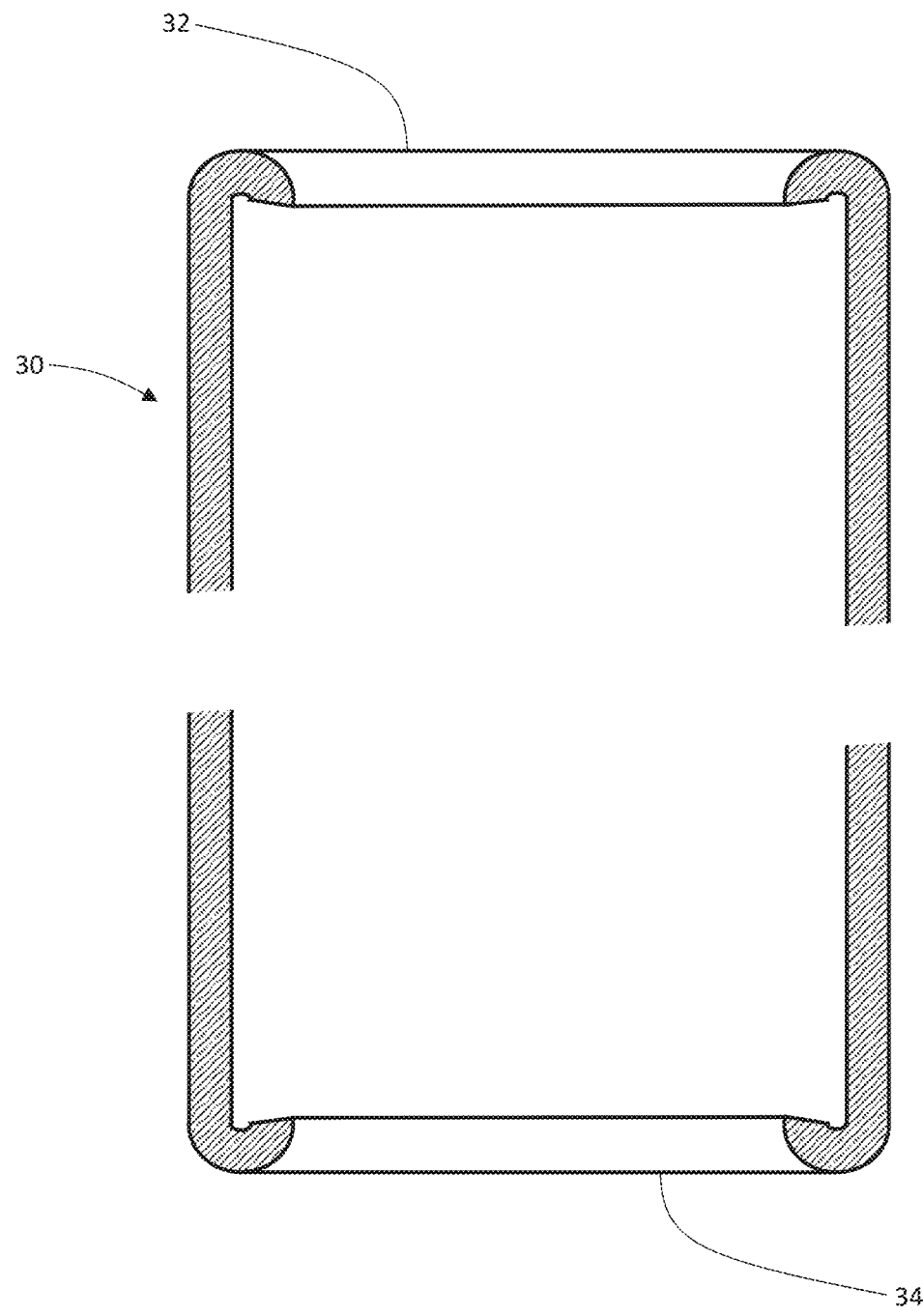
FIG. 3B is an expanded longitudinal cross section of an example of an ejection plunger portion of the tampon product of FIG. 1, taken through line 3-3 identified in FIG. 2A.

As suggested in FIG. 3A, barrel portion 12 may be sized to house a tampon pledget 52 in its self-sustaining form. It may be desired that barrel portion 12 have an inner diameter that is small enough relative the outer lateral dimension of pledget 52 such that pledget 52 cannot freely slide longitudinally within barrel portion 52 (due to slight interference or radial compression and light static friction resistance), but not so small as to create unacceptable static friction resistance and thereby require the user to exert unacceptably great longitudinal force on ejection plunger 30 to eject pledget 52 from barrel portion 12, when ejection is desired.

Also as suggested in FIG. 3A, it may be desired that ejection plunger 30 have an outer lateral/radial diameter (of its cylindrical form) that is equal to or smaller than the inner diameter or other inner lateral dimension of barrel portion 12. It may be desired to provide such clearance within 1% of parity such that ejection plunger 30 cannot freely and unintentionally slide coaxially/longitudinally within or out of barrel portion 12 in the absence of intentionally applied force, but such that the force required to slide ejection plunger 30 within barrel portion 12 is not so great as to be unacceptably great to the user, or even potentially destructive to the applicator.

Still referring to FIG. 3A, the ejection plunger 30 may be provided with an inner diameter that is smaller than the outer diameter or lateral dimension of the tampon pledget 52 (or other object) housed within the barrel portion 12. With this size relationship, longitudinal force applied to the ejection plunger 30 urging it into the barrel portion 12 will cause it forward end 32 to contact the rearward end 56 of the tampon pledget 52 (or other object) and urge the object forward and out the forward end 14 of barrel portion 12. As an alternative, or in addition to, such inner diameter size, as suggested in FIG. 3B, the forward end 32 of ejection plunger 30 may have its circumferential edge rolled over inwardly or otherwise formed to extend radially inwardly, thereby effectively reducing the inner diameter or inner lateral dimension of the ejection plunger 30 at its forward end 32, thereby increasing the amount of area at the forward end 32 of ejection plunger 30 that effectively contacts the rearward end 56 of the pledget 52 or other object within barrel portion 21, to transmit ejection force exerted by the user. A similar feature can be imparted to the rearward end 34 of ejection plunger 32 (see FIG. 3B), to expand contact surface area and decrease focused/localized pressure on the user's finger at the circumferential rim of the rearward end 34 when the user applies ejection force at the rearward end 34, and thereby make application of ejection force more comfortable to the user's finger.

The barrel portion 12 may be provided in the form of a spirally wound, convolutely wound or longitudinally seamed hollow tube which is formed from paper, paperboard, cardboard or a combination thereof. The paper, paperboard or cardboard may be manufactured predominantly of wood or cellulose pulp fiber. The barrel portion 12 may be manufactured to be relatively rigid and have an outer diameter of about 10 millimeters to about 20 millimeters. The barrel portion 12 has a wall which may be manufactured to have a predetermined thickness of about 0.1 mm to about 0.7 mm. The wall may be constructed from a single ply of material or be formed from two or more plies that are bonded together to form a laminate.

The use of two or more plies or layers is preferred for it enables the manufacturer to use particularly selected materials in the various layers that may enhance the performance of the tampon applicator. When two or more plies are included, all the plies may be spirally wound, convolutely wound or longitudinally seamed to form an elongated cylinder. The wall may be constructed using a smooth thin ply of material on the outside or exterior surface that surrounds a coarser and possibly thicker ply. When the wall includes at least three plies, the middle ply may be the thicker ply and the interior and exterior plies may be imparted with a smooth and/or slippery surface finish (e.g., via application of a coating) to facilitate expulsion of the tampon and to facilitate comfortable insertion of the barrel portion 12 into the vaginal cavity, respectively. By sandwiching a thick, coarser ply of material between two thin, smooth plies, a barrel portion 12 may be provided which is economical but functional. The wall may include one to three, four or five plies, although more plies may be utilized if desired.

The plies forming the wall may be held together by a glue, or by heat, pressure, ultrasonics, etc. The glue may be either water-soluble or water-insoluble. A water-soluble glue may be preferred, for reasons of environment-related concerns, so that the layers of the wall will readily separate when wetted by water. Such wetting may occur, for example, upon immersion by flushing in a toilet, or upon exposure to environmental moisture (for example, in an outside landfill in moist or wet conditions). When a water-soluble glue is used, exposure of the barrel portion 12 to processes of a municipal waste treatment plant, wherein soaking in water, interaction with chemicals and agitation all occur, will cause the layers of the wall to separate and disperse in a relatively short period of time. In addition to the objective of providing for dissolution and dispersibility, as noted above, it may be desirable to reduce or eliminate components derived from petroleum according to currently recognized objectives relating to use of sustainably-sourced and environmentally-friendly materials. Many (if not all) glues currently used to adhere layers of paper together to form tube structures for applicator components are aqueous formulations including polyvinyl acetate (PVAc). PVAc-based glue (exemplified by "white glue" or ELMER'S brand glue) is desirable because it is water soluble, readily penetrates pores of fibrous cellulose/wood pulp paper and adheres to cellulose fibers, is tacky when applied (promoting rapid setting and bonding), and can be formulated with relatively high water content and low viscosity for ease of application during manufacturing. However, PVAc is derived from hydrocarbons (acetylene or ethylene), most economically obtained from petroleum. Other non-petroleum-derived glue components might be considered, including hide glue and sodium silicate (water glass), used elsewhere in paper-related applications; but each has shortcomings for purposes of the present application.

Another non-petroleum-derived glue component that may be considered is starch. While having certain properties that may be deemed desirable for the present application, an aqueous preparation of starch alone does not exhibit the tackiness and rapid setting properties of PVAc-based glue when applied to paper, rendering it unsatisfactory for efficient paper tube manufacturing. It has been found, however, that inclusion of a cross linker may improve the tackiness of a starch-based glue used to bond paper layer components. One material that may be included as a cross linker is sodium aluminate, as disclosed in US 2015/0233058, wherein use in making corrugated cardboard sheet is described. A suitable starch-based glue compound may be predominantly constituted by starch by weight, and may include a minor weight fraction of sodium aluminate (in a substantially dry state, prior to addition of water or alternatively, after use in manufacturing paper tube stock, and substantial drying thereof). Through compounding, addition of water and mixing to prepare glue for use in making paper tube stock for tampon applicator components, the glue may include from 40 percent to 75 percent water by weight, or more preferably 40 percent to 65 percent water by weight, or even more preferably 40 percent to 60 percent water by weight. In some examples, the glue formulation may include from 50 percent to 60 percent water by weight.

The barrel portion may be manufactured such that the inside diameter thereof is less than about 19 mm and preferably less than about 16 mm. Although the outside diameter of typical menstrual-use tampons varies, most menstrual-use tampons currently marketed have an outside diameter of less than about 19 mm. However, if one desires to use applicator of the present disclosure for purposes other than delivery of a menstrual-use tampon to a human female vaginal cavity (such as, for example, delivery of other devices, medications, etc. to other cavities in humans, or cavities in animals (veterinary use)), a barrel portion 12 with a larger diameter may be desired.

The material may be overlapped into a tubular configuration. Spirally or convolutely winding the barrel portion 12 into a cylindrical tube is especially advantageous when the barrel portion 12 is formed from a laminate. The reason for this is that when a laminate is circumferentially wound into a tube and a butt seam or an overlap is formed, a common problem with a rigid or stiff walled, tubular member having a relatively small diameter and a butt seam is that the seam may tend to come apart after formation if exposed to certain stress forces and/or high humidity. Accordingly, it may be preferred that the barrel portion 12 be formed into a cylindrical configuration without the presence of a butt seam or an overlap.

The ejection plunger 30 may be manufactured of similar materials and in a similar layered and wound configuration as barrel portion 12, with appropriate adjustments to its size (length and outer diameter) to enable it to fit within barrel portion 12 with appropriate clearance, and have sufficient length to facilitate full ejection of the tampon pledget (or other object) from barrel portion 12.

For a menstrual-use tampon, the barrel portion 12 may be sized and configured to snugly house the tampon. As noted above, it may be desired that the barrel portion 12 have a relatively smooth exterior surface that will facilitate comfortable insertion of the barrel portion 12 into the vaginal cavity. When the exterior surface is smooth (and preferably has surface properties and/or surface treatment that provide appropriately low friction with sensitive tissue), the barrel portion 12 will easily slide within the vaginal cavity without subjecting the internal tissues of the vagina to irritation or abrasion. The exterior surface of barrel portion 12 may be coated to give it appropriate low friction characteristic surface properties. Wax, polyethylene, a combination of wax and polyethylene and cellophane are representative components of coatings that have been applied in the art, to barrel portions of tampon applicators, to facilitate comfortable use.

When tube stock used to form an applicator or ejection plunger is formed of paper (in turn, formed of cellulose pulp such as wood pulp), prior to coating the material may be relatively hydrophilic, porous and absorbent, and also, potentially abrasive to sensitive tissue. The hydrophilic, porous and absorbent qualities may cause the paper material to draw moisture from moist tissues, and thereby increase the potential for irritation and abrasion from sliding contact therebetween. Additionally, these qualities may increase the potential for staining of the paper material with menstrual fluid, which, following withdrawal of an applicator from the vaginal cavity, some users may find undesirable. Accordingly, it may be desirable to apply a coating to the material that, when in melt and/or liquid form readily penetrates the fibrous structure of the paper and seals it to prevent it from absorbing fluid.

Additionally, it may be preferred that the coating itself have hydrophobic surface properties so as to feel lubricious against moist tissues. The coating is, desirably, easily and efficiently applied to the paper stock. Further, it should have a melting temperature that is not so low such as may cause it to melt when the product is transported and/or stored in hot environmental conditions (e.g., during transport/shipment in hot weather). The coating should be non-toxic and biocompatible.

Paraffin wax has these desirable characteristics, and has been conventionally used to coat finished paper materials used to make outer layers of tampon applicators, to provide a suitable surface finish that is non-absorbent and sufficiently lubricious for comfortable use. Paraffin, however, is derived from petroleum. As noted in the Background, increasing regulatory and market pressures are driving searches for uses of materials other than materials derived from or containing petroleum, for making disposable consumer products.

As an alternative to a wax derived from petroleum, various natural waxes might be considered as substitutes, including but not limited to animal waxes including beeswax, Chinese wax, lanolin, shellac wax, spermaceti; and vegetable waxes including but not limited to bayberry wax, candelilla wax, carnauba wax, castor wax, esparto wax, Japan wax, jojoba wax, ouricury wax, rice bran wax, soy wax, sunflower wax and tallow tree wax.

The natural wax may be selected for having particular properties desired. For coating paper stock that will be rolled onto a supply roll for transport and storage prior to use to manufacture tube stock, a wax that will resist transfer from a coated surface to an uncoated surface when placed in contact therewith may be desired. Accordingly it may be desired that the selected wax resist contact transfer at temperatures and under conditions of manufacture, shipping and storage contemplated herein. This characteristic is deemed desirable because hydrophobic wax disposed on the uncoated side of the paper can obstruct penetration and adhesion of a water-based glue on the uncoated side, during tube manufacturing. Relative non-transferability under the conditions contemplated herein is believed to be a result of the relatively higher softening and melting temperatures, and hardness, of certain vegetable waxes as compared with, for example, beeswax. For this reason, natural waxes having comparatively higher softening and melt temperatures may be preferred, e.g., candelilla wax, sunflower wax, shellac wax, rice bran wax, castor wax and carnauba wax. Particular waxes from among these may also be preferred for consistency and whiteness of color. Without intending to be bound by theory, it is believed that users of tampons provided in paper/cardboard applicators prefer applicators that are white, over applicators of an off-white or darker color, because white color tends to have the effect, with respect to consumer perceptions, of connoting hygienic purity and cleanliness. A suitable vegetable wax formulation that has been identified is NOWAX CW 6120, a product of Paramelt B. V., Heerhugowaard, Netherlands, which exhibits desirable properties for purposes herein including relatively higher softening and melt temperatures, non-transferability via contact, and whiteness of color.

It might be thought that one or more of the natural waxes or formulations thereof identified above may satisfy some or all of the objectives associated with the desire to eliminate petroleum-based wax, and so might be deemed suitable substitutes for paraffin. It has been discovered, however, that a simple substitution of a natural wax for paraffin wax to form a coating can have unexpected and undesirable consequences that render the resulting coated product unsuccessful.

It has been discovered that a simple substitution of a natural wax for paraffin may cause a failure on an applicator manufacturing line, when the applicator components were cylindrical in form and had an outer surface formed of the wax coating. More particularly, it has been discovered that applicator components (e.g., barrel portions) coated with a vegetable wax (e.g. the Paramelt product identified above) will not slide freely against one another, causing them to fail to move in orderly sequential fashion through a processing line. In several experimental runs on conventional manufacturing equipment, applicator components coated with the Paramelt wax formulation failed to slide freely against each other when sequentially rolled and conveyed, and as a result, unintentionally piled up and accumulated in one section of the line, causing a line failure and necessitating a shutdown. Without intending to be bound by theory, it is believed that a combination of comparatively greater tackiness of the wax surfaces and/or excessive friction between sequential applicator components moving through the line caused the failures.

Additionally, it has been learned that applicator components coated with a natural wax may have an unacceptably tacky feel to consumers when manipulated between the fingers.

Figure 4:
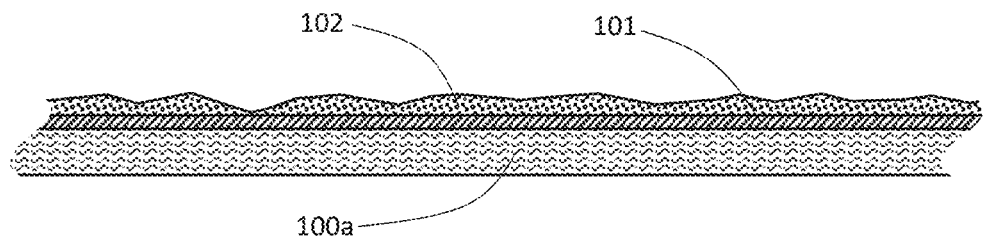
FIGS. 4-7 are schematic cross sections of various examples of coated paper layers, taken along planes oriented along a z-direction relative the layers.
Figure 5:
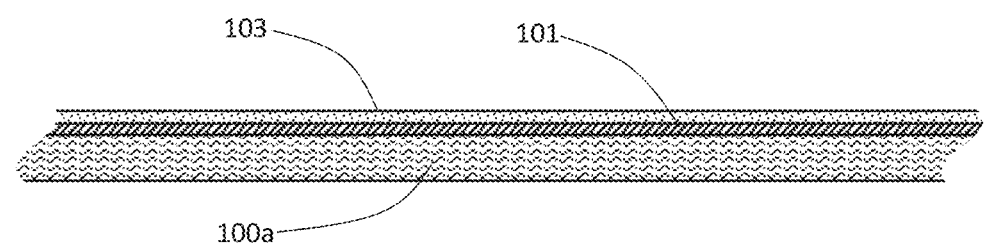

Through further investigation and experimentation it has been discovered that the surface finish appearing on a paraffin wax-coated paper of a particular composition was more irregular (i.e., had greater surface texture) at a microscopic level, than that of paper of the same composition, coated with the Paramelt vegetable wax composition. Referring to FIG. 4, a conventional coated paper (to be used to form the outer layer of applicator components), including a smooth-calendered substrate paper layer 100a, a whitening pre-coating layer 101 including latex and a whitening agent (a clay), and a paraffin wax coating 102 is schematically illustrated. The formulation of the latex pre-coating layer 101 also provided a smooth surface finish beneath the wax coating. In FIG. 5, the same latex-coated paper composition and configuration is schematically illustrated, but a vegetable wax coating 103 of the Paramelt wax composition has been substituted for the paraffin wax coating 102. Comparison of FIGS. 4 and 5 schematically illustrates the differences in results, which were discovered through experimentation and observation. It was observed that the Paramelt wax composition coating provided a comparatively smoother, glossier and less textured surface finish (schematically illustrated in FIG. 5).

Without intending to be bound by theory, it is believed that the greater microscopic surface texture appearing on the paraffin wax-coated paper (schematically illustrated in FIG. 4) is a result of the particular crystal structure of paraffin wax. By contrast, the vegetable wax composition flows and hardens to comparatively smoother (less textured) coating surface finish (schematically illustrated in FIG. 5). The glossier surface finish provided by the vegetable wax coating was deemed visually more appealing than the comparatively more dull finish provided by the paraffin coating, but as noted, applicator components with the same paper substrate with the vegetable wax coating were problematic on the manufacturing line. Without intending to be bound by theory, it is believed that the greater microscopic surface texture inherent in the paraffin wax coating results in fewer/lesser areas of contact between the surface of the coated paper and adjacent objects contracting the surface—because the adjacent objects contact the paraffin wax-coated surface only at the outermost/uppermost ridges or tops of the surface features (relative the Z-direction). This comparatively lesser contact surface area is believed to comparatively reduce relative sliding resistance between two contacting objects in which one or both objects have a surface formed of the same paraffin wax-coated paper.

Figure 6:
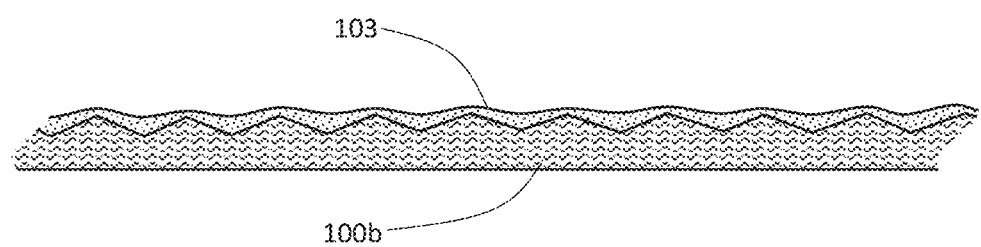
Figure 7:
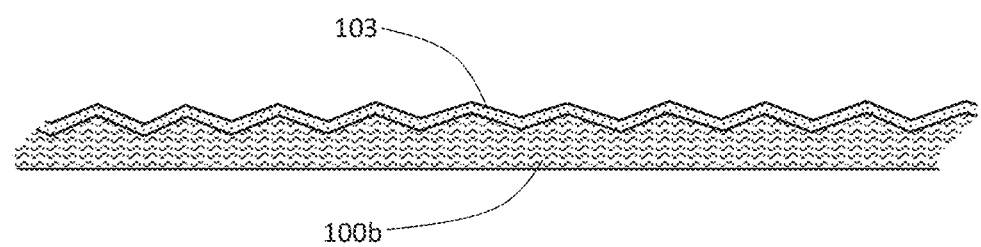
Figure 8C:
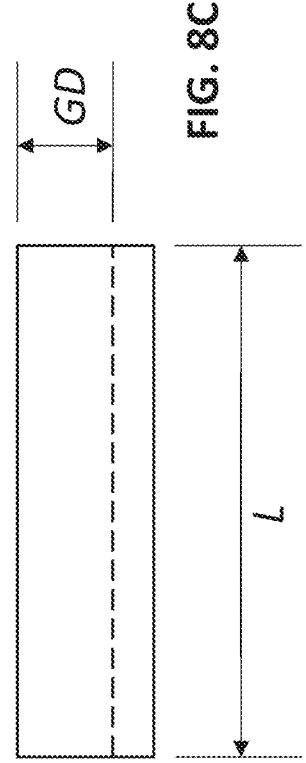
FIGS. 8A-8C are top, end and side views, respectively, of a sample fixture used in the Relative Sliding Resistance Coefficient Measurement (CSR) and Gripping Slip Resistance Coefficient (CGSR) Measurement methods described herein.
Figure 8A:
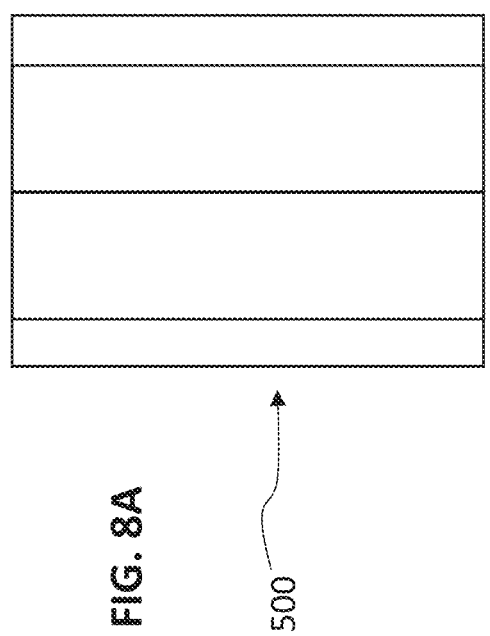
Figure 8B:
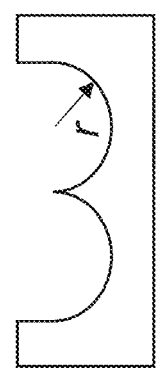
Figure 9:
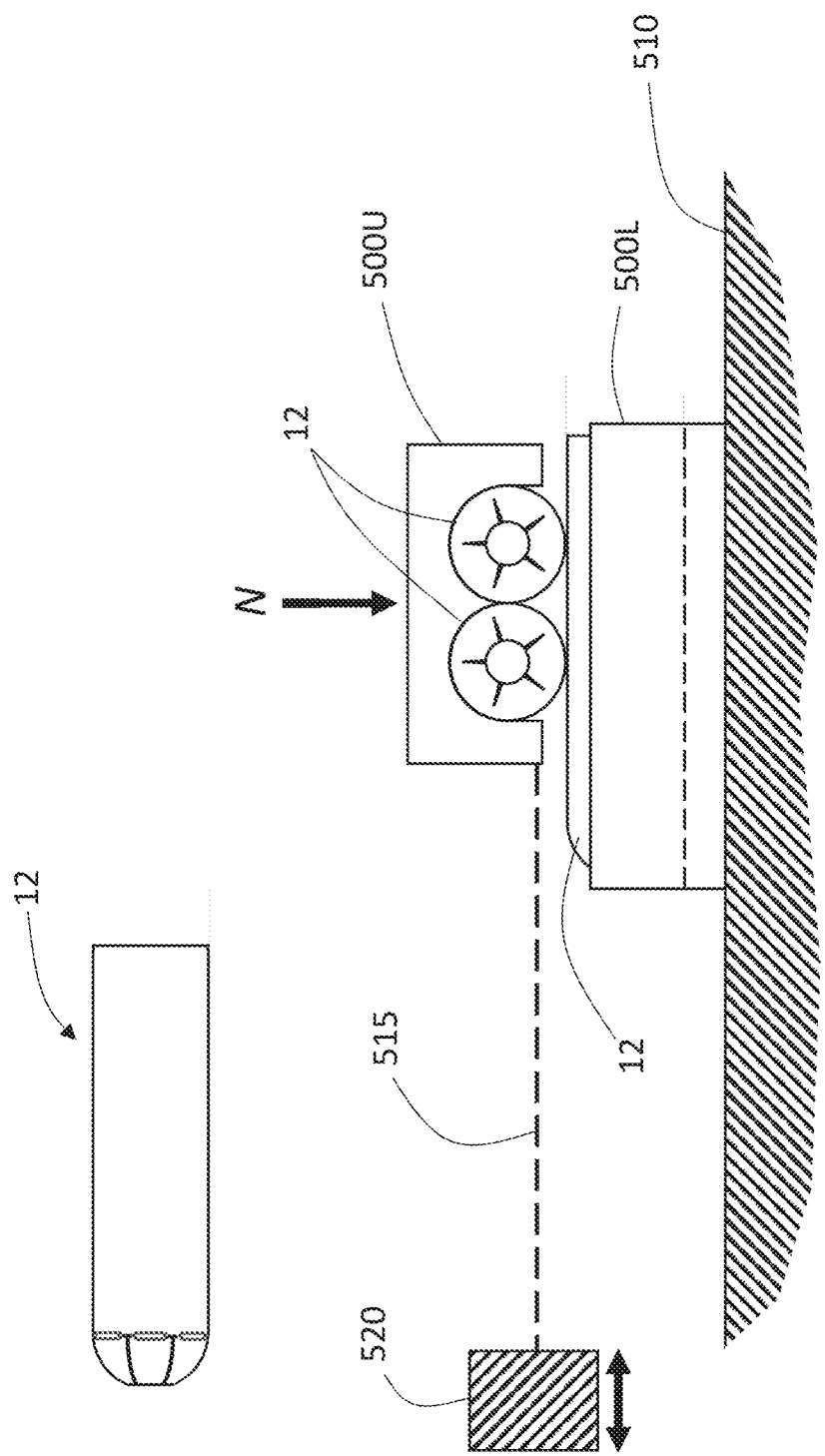
FIG. 9 is a schematic side view depiction of equipment and test sample arrangement for use in the Relative Sliding Resistance Coefficient Measurement Method described herein.
Figure 10:
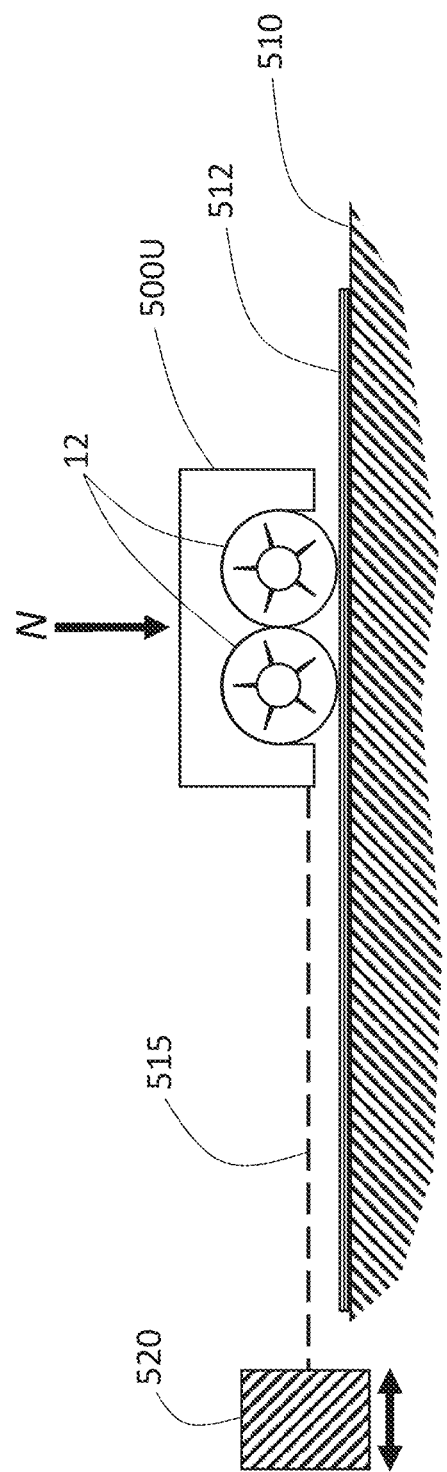
FIG. 10 is a schematic side view depiction of equipment and test sample arrangement for use in the Gripping Slip Resistance Coefficient Measurement Method described herein.

Referring to FIGS. 6 and 7, it has been discovered that, to produce a suitable surface texture in a paper coated with natural wax (or other material) that approximates the presence and effects of the texture inherently produced by a paraffin wax coating, the manufacture of the substrate paper layer 100b itself may be manipulated and adjusted, via manufacturing technique and equipment selection, so as to provide suitable surface texture in the paper layer itself. If the paper layer 100b, as the substrate, is manufactured with a suitable surface texture, and excessively smoothing processes (e.g., smooth roll calendering) or intermediate overlying smoothing coatings are included, a highly flowable, smooth-finishing coating will tend to follow and reflect the underlying texture of the substrate paper to some extent. A suitable texture may be imparted to the paper substrate via selection of the compressing felt and/or screen mesh used to form the paper and/or surface texture features of calender rollers used to calender and finish the paper stock. Other techniques for imparting a textured finish to paper, such as creping, are known. Following calendering and/or other consolidation/finishing, the textured paper may be coated with suitable wax or other material via, for example, use of a kiss roll coating system.

In order to coat a paper substrate, to be used as an outer layer of a paper tampon applicator component, wherein the coating is not formulated predominantly of paraffin or another material derived from petroleum, and to provide for uninterrupted manufacturability on conventional tampon applicator manufacturer lines, it may be desired to adjust the surface texture of the uncoated paper substrate to achieve component-to-component Relative Sliding Resistance Coefficients (CSRs) within appropriate ranges proximate to those exhibited by components having conventional paraffin wax coating.

Table 1 below reflects results of measurement of CSRs (static and kinetic) for various applicator barrel portion samples:

Sample Configuration 1 was a sample of a cardboard barrel portion of an applicator currently provided with TAMPAX Cardboard brand tampons, having paraffin wax coating 102. The outer paper layer of the sample had a configuration schematically illustrated in FIG. 4.

Sample Configuration 2 was a sample in which a latex-coated paper substrate of the same configuration and composition of the outer layer of the barrel portion of Sample Configuration 1, but having a vegetable wax (Paramelt NOWAX CW 6120) coating 103 substituted for a paraffin wax coating 102, had been wrapped about a barrel portion similar to that of Sample Configuration 1 for purposes of study. The wrapping paper layer had a configuration schematically illustrated in FIG. 5.

Sample Configurations 3 and 4 were samples of the same pulp paper composition of the barrel portion of Sample Configuration 1, except: (1) the whitening pre-coating layer 101 on the outer paper layer was omitted; (2) the surface texture of the outer paper surface had been adjusted/increased prior to coating, in the manufacturing process; and (3) the Paramelt wax coating 103 was substituted for a paraffin wax coating 102.

For Sample Configuration 3, the wax temperature in the wax bath of the kiss roll coating system was regulated to 135 C, and the basis weight of the wax deposit on the paper was regulated to 3.5 gsm, by location of a doctor blade relatively farther downstream of the kiss roll coater.

For Sample Configuration 4, the wax temperature in the wax bath of the kiss roll coating system was regulated to 105 C, and the basis weight of the wax deposit on the paper was regulated to 2.5 gsm, by location of a doctor blade relatively nearer downstream of the kiss roll coater.

As suggested and schematically illustrated in FIGS. 6 and 7, it was observed that the vegetable wax coating 103 applied from the relatively greater temperature wax bath in the kiss roll system (Sample Configuration 3) tended to flow more freely to result a relatively smoother/less prominently textured surface finish. It was also observed that the vegetable wax at greater temperature (and as a result, lower viscosity) more deeply penetrated the porous paper substrate in the z-direction prior to cooling/hardening. This might be deemed undesirable in some circumstances; if wax impregnates the paper substrate to the extent that it entirely penetrates the paper through to the underside surface of the substrate (opposite the coated side), the wax, being hydrophobic, can interfere with glue penetration and adhesion between paper layers during the subsequent tube formation/gluing process, when water-based glue is used. For this reason and also due to the lower sliding resistance coefficients achieved, Sample Configuration 4 (having comparatively more pronounced surface texture and less wax penetration into the paper) was deemed the more preferred example, among Configurations 3 and 4.

It can be seen from the data that CSRs increased for Sample Configuration 2, to values substantially higher than those for Sample Configuration 1, while CSRs decreased for Sample Configurations 3 and 4, to values comparable or lower than those for Sample Configuration 1. Applicator tube stock having Sample Configuration 1 (current market) and Sample Configurations 3 and 4 (experimental) ran successfully in test applicator manufacturing runs conducted by Applicants, while applicator tube stock manufactured to have an an outer layer of the wrapping paper of Sample Configuration 2 (experimental) caused unintended pile-up and accumulation of applicator components and necessitated a line shutdown as described above. Tube stock of Sample Configuration 4 ran the most smoothly on the line; this is believed to have been the result of its comparatively more pronounced surface texture and resulting, comparatively lower, CSRs.

TABLE 1

| Sample Configuration | Sample Description | Static CSR | Kinetic CSR |
|---|---|---|---|
| 1 | Current Mkt Substrate + Paraffin Wax Coat | 0.172 ± 0.018 | 0.149 ± 0.003 |
| 2 | Current Mkt Substrate + Vegetable Wax Coat | 0.363 | 0.354 |
| 3 | Modified Substrate + Vegetable Wax Coat (wax applied at relatively higher temperature) | 0.202 ± 0.009 | 0.163 ± 0.002 |
| 4 | Modified Substrate + Vegetable Wax Coat (wax applied at relatively lower temperature) | 0.163 ± 0.011 | 0.147 ± 0.002 |

Based on observations in experimental manufacturing runs, and the data collected above, Applicants have determined that when manufacturing a paper substrate, to be used as an outer layer of a paper tampon applicator component, wherein the coating is not formulated predominantly of paraffin or another material derived from petroleum, it may be desired to adjust the surface texture of the uncoated paper substrate to achieve/result in a textured surface that approximates the effects of a paraffin wax coating. It is believed that those effects are successfully approximated when the surface texture of the substrate paper is adjusted such that the coated paper results in a component-to-component static CSR no greater than 0.250, preferably no greater than 0.230, and more preferably no greater than 0.210, or 0.200, or even 0.190. In combination, or alternatively, and for similar reasons, it may be desired that the coated paper results in a component-to-component kinetic CSR no greater than 0.210, preferably no greater than 0.190, and more preferably no greater than 0.175, or 0.165, or even 0.160. In some examples, such coefficients may be achieved using a natural wax coating (including, predominantly, formulations of one or more natural waxes identified above) applied to a suitably calendered or otherwise suitably finished/textured paper substrate. In a more particular example, such coefficients may be achieved using a wax coating predominantly constituted by vegetable wax, applied to a suitably finished/textured paper substrate. The CSRs are believed to be important factors for success in manufacturing tampon applicator components from paper tube stock, on conventional equipment. The wax formulation and paper surface texture have effects on the values of those coefficients, and may be selected and/or adjusted to result in coefficients that are sufficiently low as described above. Based on the data collected, it is believed that static and kinetic CSRs for a coating constituted of a vegetable wax formulation as low as 0.160 and 0.145, respectively, if not lower, might be achieved. It is believed that combinations of substrate paper texturing and coating formula modifications might be available to reduce these coefficients even further, for example, to 0.150 and 0.135, or 0.140 and 0.125, or even lower values, respectively. It is noted, however, that when making a substitution for paraffin wax as a coating for a paper tampon applicator component, the fact that CSRs should be below one or more particular thresholds as identified herein, is deemed to be one aspect of the discovery—and not that any particular combination of substrate paper surface texture or particular coating constituent or formulation is required. The components and constituents identified and described herein are only deemed examples.

Figure 11:
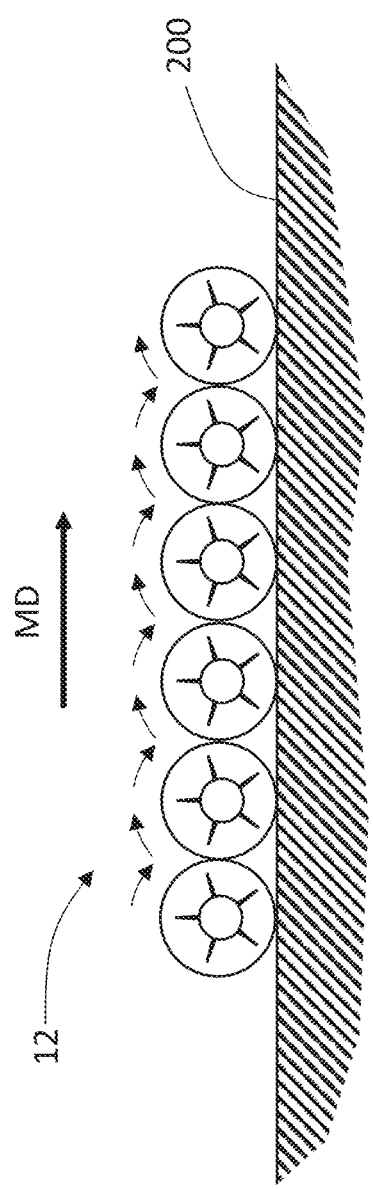
FIG. 11 is a schematic cross direction view depiction of a portion of a tampon applicator component processing line.

As suggested above, many manufacturing systems currently in use, for manufacturing and/or processing components of tampon applicators 10 formed of cut lengths of rolled paper or rolled cardboard, include an apparatus for conveying or translating the applicator components (e.g., barrel portions 12 and/or ejection plungers 30), in their precursor or finished forms, along a processing/manufacturing/assembly line. Alternatively or in addition, many tampon product assembly systems currently in use include an apparatus for conveying or translating the applicator components (e.g., barrel portions 12 and/or ejection plungers 30), in their precursor or finished forms, along a processing/manufacturing/assembly line. Referring to FIG. 11, such systems typically involve conveyance or translation of components such as barrel portions 12 and/or ejection plungers 30 (or cut lengths of paper tube stock constituting precursors to components 12 and/or 13, having coated outer surfaces) in a machine direction MD along a guiding and/or conveying and/or collecting surface 200. For smooth operation such systems often require the applicator components to roll freely therealong as suggested in FIG. 11. As they are urged along a machine direction MD, the longitudinal axes of the moving components will typically be aligned substantially perpendicularly to the machine direction MD at one or more locations along the system and substantially in parallel with a cross direction (with respect to FIG. 11, normal to the plane of the page). Also as suggested in FIG. 11, in many such systems the applicator components 12 and/or 30 (or cut length precursors thereof) will contact each other along their respective cylindrical surfaces as they are being conveyed or translated, and may be required to slide circumferentially against each other. If the relative contact sliding resistance between sequential components is too high, such that they do not freely slide circumferentially against each without sufficient freedom, they can be caused to stick, jump and/or back up and accumulate at a location within the system in an unintended location and/or manner, and cause a system malfunction, requiring a shutdown. It is in such systems that CSRs, controlled to be at or below certain thresholds as discussed above, may be particularly beneficial.

With respect to another aspect of the discovery, in addition to affecting tube-to-tube relative sliding resistance, surface texture and friction/slidability characteristics of a coated applicator component may be perceived positively or negatively by consumers. On one hand, consumers may prefer that the applicator not be too slippery between the fingers, because this may make manipulation of the applicator more difficult. On the other hand, consumers may negatively perceive an applicator component that feels too tacky between the fingers. It has been discovered that a suitable balance may be found between these two extremes, and that that balance can be present for a coated applicator component having CSRs below the acceptable thresholds identified above. Although for manufacturing purposes, it may be posited that relatively low static and kinetic gripping slip resistance might correlate to some extent with relatively low static and kinetic relative sliding resistance of applicator tube stock, if the applicator components in the finished product are perceived consumers as too slippery between the fingers, consumers may find them unsatisfactory. Accordingly, the manufacturer may wish to adjust the surface texture of an applicator component in the paper manufacturing process as described above, to adjust for gripping slip resistance as measured by the Gripping Slip Resistance Coefficient (CGSR) Measurement Method described below.

Table 2 below reflects results of measurement of CGSRs (static and kinetic) for the various applicator barrel portion samples described above.

It can be seen from the data that CGSRs increased for Sample Configuration 2, to values substantially higher than those for Sample Configuration 1, while CGSRs decreased for Sample Configurations 3 and 4, to values comparable or lower than those for Sample Configuration 1. Based upon consumer acceptance of current market applicators (e.g., Sample Configuration 1), applicator tube stock having Sample Configurations 3 and 4 (experimental), exhibiting comparable values, were deemed by inventors to be have acceptably high CGSRs (i.e., they are deemed to be not too slippery) for a satisfactory consumer usage experience. Based on the Inventors' experience it is believed preferable, however, that paper applicator components such as a barrel portion 12 and/or an ejection plunger 30 exhibit CGSRs no less than 0.190 (static) and/or 0.170 (kinetic), more preferably no less than 0.200 (static) and/or 0.180 (kinetic), and even more preferably no less than 0.210 (static) and/or 0.190 (kinetic).

TABLE 2

| Sample Configuration | Sample Description | Static CGSR | Kinetic CGSR |
| --- | --- | --- | --- |
| 1 | Current Mkt Substrate + Paraffin Wax Coat | 0.231 ± 0.026 | 0.173 ± 0.007 |
| 2 | Current Mkt Substrate + Vegetable Wax Coat | 0.282 | 0.284 |
| 3 | Modified Substrate + Vegetable Wax Coat (wax applied at relatively higher temperature) | 0.220 ± 0.003 | 0.214 ± 0.007 |
| 4 | Modified Substrate + Vegetable Wax Coat (wax applied at relatively lower temperature) | 0.226 ± 0.005 | 0.203 ± 0.003 |

Persons of ordinary skill in the art will understand that suitably coated paper applicator components may be manufactured to have static and kinetic CGSRs that are substantially higher than the minimum floor limits suggested above, but that these would be deemed unacceptably tacky to consumers. Without intending to be bound by theory, it is believed based on experience that static and kinetic CGSRs higher than 0.350 would be deemed unacceptably tacky in tactile feel to consumers. Without intending to be bound by theory, and noting that the respective values for CGSR and CSR differ as a result of differing interactions between differing types of surfaces, it is believed that such higher CGSR values may also correlate with unacceptably high CSR values in tampon applicator component coated paper tube stock.

The applicator of the present disclosure may be used for the delivery of menstrual-use devices, such as a tampon, an intravaginal collection device (e.g., menstrual cup), and interlabial pads. The applicator of the present disclosure may be used for the delivery of a pessary. The applicator may also be useful for delivery of oral, rectal, and vaginal suppositories, as well as nasal devices, such as nasal tampons. The applicator may be used for delivery of various other materials including, medicaments, moisturizers, vitamins and minerals, spermicides, and odor controlling agents. These materials may be delivered in the form of rigid solid objects, deformable solid objects, creams, foams, gels, etc. The applicator may be adapted for human or animal/veterinary use.

Tampon Pledget and Withdrawal Cord

Referring to FIG. 3A, a non-limiting example of a tampon having a pledget 52 in a self-sustaining form and having a forward end 54 and a rearward end 56 and a withdrawal cord 58 attached to the pledget and extending rearward from a location proximate the rearward end 56 of the pledget 52. Generally, the "pledget" as referred to herein is that portion of the tampon that includes the main body and mass of absorbent material, but does not include withdrawal cord 12. Tampons contemplated herein, however, are not limited to structures having the particular configuration shown in the drawing.

The pledget 52 of the tampon as shown in FIG. 3A has a forward end 54 and a rearward end 56. During manufacture of the tampons the pledget may be folded, bunched, compressed and/or otherwise formed in size and shape, from its initially manufactured configuration into a generally cylindrical and/or capsule-shaped configuration (e.g. as shown in FIG. 3A) along a radial direction, the lateral direction, longitudinal direction, or in some combination thereof.

While the pledget may be formed into a substantially cylindrical and/or capsule-shaped configuration a suggested in FIG. 3A, other shapes are also possible. These may include shapes having a lateral cross section which may be described as oval, elliptical, ovoid, stadium, rectangular, triangular, trapezoidal, semi-circular, or other suitable shapes. In the example depicted in FIG. 3A, the pledget 52 may be compressed to its greatest extent, or primarily, in the lateral direction, to the shape of its self-sustaining form. (For purposes herein, a "primary" direction of compression is the direction along which greatest displacement of the pledget body occurs, in the transition from its uncompressed form to its compressed, self-sustaining form.) The means of lateral compression may induce the pledget to fold up in a z-direction relative the pledget material prior to compression, as the side edges thereof are urged laterally toward the longitudinal axis. The pledget may be compressed laterally to a self-sustaining form by use of equipment and processes described in, for example, US2005/0027275 and/or US2008/0262464.

The pledget contemplated herein may have any other suitable form and structure. Other non-limiting examples of suitable pledget forms, material composition and structure are depicted and described in US2010/0268182 and US2007/0260211.

In the non-limiting example depicted in FIG. 3A, pledget 52 may include a batt or other mass of absorbent material, disposed within an outer cover (not specifically shown). This type pledget may be formed on a continuous processing line wherein absorbent fibrous material is continuously deposited (e.g., via an airlaying process) to form a continuous batt having a desired cross-direction width and depth/weight, onto a continuous web of cover material being conveyed along a machine direction. The cover material web may then be wrapped about the batt by suitable web guiding and folding equipment, to form a continuous wrapped batt. Individual pledgets may then be cut from the continuous batt by repetitive die cutting across the moving batt. The cross-direction cuts may be linear, which will result in rectangular pledgets. Alternatively, in some examples, the cross-direction cuts may be non-linear; the cutting tool may be configured to make cuts forming the respective edges of each successive pledget, to impart the edges with respective non-linear, e.g., arched or curved, profiles. In such examples, a curved forward/rearward edge profile may help facilitate subsequent compression and formation into a cylindrical or capsule-shaped form with rounded or otherwise tapered forward and rearward ends, through a graduating reduction or tapering down, via the cut profile, in the bulk/quantity of material that must be compressed at forward and rearward ends 54, 56. Various shapes that embody a tapering down of the quantity of material present toward the forward and rearward ends of the pledget are contemplated.

In some examples (not specifically shown), the pledget 52 may have a laminar structure including integral or discrete layers. As noted, the pledget 52 may include an enveloping cover and one or more layers of absorbent material positioned within the cover. In other examples, the pledget need not have a layered structure at all. To facilitate compression into its self-sustaining form the pledget may be folded (e.g., as in currently marketed TAMPAX brand tampons, a product of The Procter & Gamble Company, Cincinnati, OH); may be rolled (e.g. as in currently marketed U BY KOTEX brand tampons, a product of Kimberly-Clark Worldwide, Inc., Irving, TX); may comprise a "petal" structure (e.g. of overlaying/underlaying, crossing rectangular patches of absorbent material, in a configuration present in PLAYTEX SPORT brand tampons, a product of Edgewell Personal Care LLC, Chesterfield, MO); or any other of the structures and configurations which are known in the art relating to tampon pledgets and their manufacture and consolidation to self-sustaining forms.

The pledget 52 may include a wide variety of liquid-absorbing materials commonly used for absorbency in absorbent articles, such as but not limited to rayon fiber, cotton fiber, wood pulp fiber and comminuted wood pulp fiber (sometimes called "airfelt"). Examples of other suitable absorbent materials may include creped cellulose wadding; spun and/or meltblown polymer fibers or filaments; chemically stiffened, modified or cross-linked cellulosic fibers; other synthetic fibers such as polyamide fibers (e.g., nylon fibers); peat moss; absorbent foams (such as open-celled foam formed through polymerization of a high internal phase water-in-oil emulsion); nonwoven web materials of natural and/or synthetic fibers or combinations thereof, tissue including tissue wraps and tissue laminates; or any equivalent material or combinations of materials, or blends or combinations of these. Suitable fibers include rayon. (Herein, the term "rayon" is used generically to refer to fibers spun from regenerated cellulose, and includes, but is not necessarily limited to, viscose, MODAL, TENCEL (or lyocell); tri-lobal and conventional rayon fibers, and needle punched rayon). Suitable cotton fibers may include long fiber cotton, short fiber cotton, cotton linters, T-fiber cotton, card strips, and comber cotton. Preferably, the cotton fibers or fabric layer thereof should be scoured (for removal of natural hydrophobic waxes and impurities) and bleached (for whiteness) and may be imparted with a glycerin finish (for enhancing compaction), a leomin finish (for lubricity), or other suitable finish. Additionally, superabsorbent materials, such as superabsorbent polymers or absorbent gelling materials may be incorporated into the pledget. In particular examples it may be desired that rayon or cotton or a blend thereof, constitute the greater proportion (by weight) of the absorbent material; that cotton alone constitute the greater proportion (by weight) or substantially all of the absorbent material, or that rayon alone constitute the greater proportion (by weight) or substantially all of the absorbent material, since rayon fibers may possess absorbency properties or capacity greater than those of other fibrous materials, per unit weight and/or per unit cost.

In the example depicted in FIG. 3A, the pledget 52 may be formed of a body or batt of soft absorbent fibrous material such as rayon fibers or cotton fibers or a combination or blend thereof, and a cover may be formed of a woven, knitted or nonwoven web fabric material of suitable composition. The materials for the body of absorbent material may have the form of nonwoven or woven fabric or a batt formed by any suitable process such as airlaying, carding, wetlaying, hydroentangling, or other known fiber deposition and consolidation techniques. For purposes of minimization of use of materials derived petroleum, it may be preferred that pledget 52 be formed predominantly, substantially or entirely of fibrous materials selected from the group consisting of cotton, rayon (or viscose, lyocell or other fibrous material spun from regenerated cellulose) or wood pulp, and combinations thereof.

As noted, the absorbent material of the pledget 52 may be surrounded or wrapped by a liquid permeable cover. Cover materials may include rayon, cotton, spunbond monocomponent, bicomponent or multicomponent fibers spun from polymer resins, or other suitable natural or synthetic fibers known in the art. If the pledget 52 is layered, respective layers may include respectively different materials. For instance, a cover, may be constituted primarily of rayon, while the absorbent material within the cover may be constituted primarily of cotton. In other examples a cover may be constituted primarily of cotton, and the intermediate layer or layers may be constituted primarily of rayon. Optionally, the entire pledget 52 may be formed of a uniform or nonuniform blend of materials throughout. In another particular example, a cover may be formed of a nonwoven web of spunbond fibers. The spunbond fibers may be spun from, for example, polymer resin including polyolefins such as polypropylene, polyethylene, or a blend or combination thereof. In a more particular embodiment the spunbond fibers may be spun bicomponent fibers including a first polypropylene resin component and a second differing polypropylene resin component or a polyethylene resin component. When formed of ordinarily hydrophobic materials such as polyolefins (including polypropylene and polyethylene) cover 30 material may be treated, e.g., by application of a suitable surfactant, to render it hydrophilic, so that it will readily attract and permit aqueous fluid to wick therethrough to the absorbent material within the cover. A nonwoven web material formed of polymeric material as described may be desired to form the cover, over natural fibrous materials or semi-synthetic rayon, for reasons of having a soft, smooth and comfortable feel and low friction against sensitive skin and internal tissues, relatively low cost and suitable wet structural/mechanical integrity. In some circumstances, however, it may be desired that the nonwoven web material forming outer cover 30 be composed of a blend of fibers selected for having differing properties, to be combined in a material having a complementary or synergistic combination of properties when these materials form an outer cover covering the absorbent material of the pledget. Generally, it may be desired that the absorbent material of the pledget have a greater attraction for (aqueous) menstrual fluid, than the nonwoven material forming the outer cover. While it will be desired that the material of the outer cover attract and wick fluid so as to capture the fluid upon contact and then distribute it along/across the surface area of the underlying absorbent material, it will also be desired that the absorbent material be able draw the fluid from the outer cover, i.e., that the outer cover not have a greater affinity for/tendency to retain the fluid therewithin, rather than surrender it to the absorbent material (where it will, desirably, be stored for the duration of use of the tampon). Thus, it may be desired that the nonwoven web material forming the outer cover be composed of a material or combination of materials that will cause the outer cover to wick fluid therealong, but also to surrender it to the absorbent material. Accordingly, in examples in which rayon (a highly hydrophilic and absorbent fibrous material) constitutes a predominant weight proportion of the absorbent material, it may be desired that rayon constitute a lesser weight proportion of the nonwoven web material forming outer cover. In particular examples, a predominant weight proportion of the absorbent material may be rayon, and nonwoven web material forming outer cover may be composed of a blend of rayon, cotton, or fibers spun from thermoplastic polymer(s), wherein the weight proportion of rayon is no greater than 67 percent, more preferably no greater than 60 percent, and even more preferably no greater than 54 percent. Toward this objective, the weight ratio of the rayon fiber to spun thermoplastic polymer fiber, or other fiber, may be from 33:67 to 67:33, more preferably from 40:60 to 60:40, and even more preferably from 46:54 to 54:46. In particular examples the thermoplastic polymer fiber may be spun from a polymer that is ordinarily hydrophobic, and selected for attributes including smoothness (low friction) and softness (pliancy) against skin and tissues. Suitable examples include polypropylene, polyester, polyethylene terephthalate (PET), polyethylene, and combinations thereof. The combination of hydrophobicity and other attributes of the polymeric fibers, with the hydrophilicity of rayon fibers, will impart desirable wicking, structural and softness characteristics to the outer cover material, while reducing the overall hydrophilicity of the nonwoven web material, so that it will readily surrender wicked fluid to the absorbent material adjacent thereto. However, as noted, for purposes of the present application it may be desired that inclusion of material derived from petroleum (such as fibers spun from polypropylene, polyethylene, polyester, etc.) be substantially if not entirely excluded.

The fiber components of the nonwoven web material forming the outer cover may be physically combined and blended, consolidated and bonded in any suitable fashion to form a cohesive nonwoven fabric material. However, it has been found that forming a web by creating a matt of blended component fibers in an airlaying or carding process, following by an entanglement process in which fibers of the matt are displaced and entangled so some extent along the z-direction, provides a web that better wicks fluid along the z-direction, as compared to a web that is not so processed. Z-direction entanglement may be imparted via processes such as, but not necessarily limited to, needling (or needle punching) and hydroentangling (as in a spunlace process). In a particular example, outer cover 30 may be formed of a nonwoven web material of which approximately 50 percent by weight is rayon fiber, and approximately 50 percent by weight is PET fiber, wherein the component fibers are carded and then hydroentangled. The web may have any suitable basis weight, but in order to balance competing objectives of mechanical strength and stability for purposes of maintaining structural integrity in processing, and suitable wicking and fluid penetrability characteristics, and material cost, it may be desired that the material be manufactured to have a basis weight of 15 gsm to 55 gsm, more preferably 25 gsm to 45 gsm, and even more preferably from 30 gsm to 40 gsm. In other examples in which processing equipment permits, a spunbond nonwoven web material spun from synthetic polymer fibers may have superior mechanical (tensile) strength per unit basis weight because the fibers are continuous rather than short/staple in length, and the spunbond material used may be of a lower basis weight, for examples, from 10 gsm to 30 gsm, more preferably from 15 gsm to 25 gsm, and even more preferably from 17 gsm to 22 gsm. In a particular nonlimiting example, outer cover 30 may be formed of a nonwoven spunbond material having a basis weight of 15 to 25 gsm, including (or even including, substantially all) fibers spun of polypropylene, and suitably treated so as to be rendered hydrophilic.

The pledget 52 in an opened configuration may have any suitable size, shape and thickness that will both provide a suitable quantity of absorbent material and resulting absorption capacity, while permitting compression into a self-sustaining form of a size and shape suitable for easy and comfortable insertion. An uncompressed, opened size similar to those of conventional currently available tampons has been found to work well. A typical size for an uncompressed pledget may be from about 2 cm to about 9 cm in longitudinal length and from about 3 cm to about 8 cm in lateral width, including any combination of length and width within those ranges, in combination with an uncompressed thickness anywhere from about 1 cm to about 3 cm. Total basis weight for a flat, uncompressed and open pledget, may be from about 150 g/m2 to about 1,400 g/m2, calculated as the weight of the pledget divided by the largest surface area on one side of the pledget. Optionally, a pledget 52 that is shorter and wider than the ranges given above may also be desired in some circumstances to promote relatively greater swelling/expansion in a lateral or radial direction during use.

A withdrawal cord 58, a configuration of which is depicted in FIG. 3A, is preferably joined to the pledget to facilitate withdrawal of the tampon from the vaginal cavity following a desired duration of use. The withdrawal cord 58 may have an attached portion attached to the pledget 52 and a free portion extending beyond the rearward end 56 thereof. In other examples, the withdrawal cord may be integral with the pledget, or an extension of a structural component of the pledget, such as of an outer cover as described above. In some examples the withdrawal cord 58 may be integral with and/or an integral extension of a skirt or wicking member included with the tampon.

In a particular example, the withdrawal cord 58 may be a separate section of cord, string, yarn, ribbon, knitted cord or strip of woven or nonwoven fabric formed separately of the components of the pledget, and then attached by any suitable mechanism to the pledget and/or to the wicking member.

The attachment mechanism may include sewing, adhesive attachment, thermal or pressure bonding, through-pledget punching, penetration and/or looping of the withdrawal cord material about structure(s) of the pledget or portions thereof, or any combination of these. An attached portion of the withdrawal cord 58 may be attached or joined to any suitable location on the pledget 11, although it may be preferable that the attachment/joining location be substantially laterally centered on the pledget and proximate to, or include a location proximate to, the rearward end 56 of the pledget, so that tensile withdrawal force in the cord, exerted by the user, acts predominantly on the rearward end of the pledget and thereby does not tend to substantially rotate or reorient the pledget within the user's body during withdrawal. In the example shown in FIG. 3A, an attached portion (not specifically shown) of the withdrawal cord 58 is joined to the pledget 11 along the length of the pledget 52, and a free portion trails free beyond the rearward end 56 of the pledget 52. The withdrawal cord 58 may be attached to the pledget 52 before the pledget is compressed to a self-sustaining form. The withdrawal cord 58 may be attached along substantially the entire length of the pledget 52.

To minimize chances of failure of the attachment between the withdrawal cord 58 and the pledget (i.e., separation) during withdrawal, it may be desired that the withdrawal cord be directly or indirectly attached along substantially the entire length of the pledget 52, thereby diffusing tensile withdrawal force exerted by the user, by distributing it over the length of the pledget. To further minimize chances of failure of the attachment, it may be desired that the attachment mechanism include a longitudinal line of stitches that penetrate the withdrawal cord 52 and the pledget 52 (through both sides), thereby connecting and affixing the withdrawal cord through a substantial portion of the structure of the pledget 52, rather than only to an outer surface thereof. Such attachment further diffuses withdrawal force through the main body/structure of the pledget. In other examples, a length of withdrawal cord stock may be threaded through a portion of the body/structure of the pledget (e.g., through a hole punched therethrough (not shown)), looped around and doubled to create pair of trailing portions (not shown). In still other examples, a length of withdrawal cord stock may be looped around a substantial portion of the pledget body without punching, and doubled to create pair of trailing portions (not shown.) The trailing portions of the pair may be tied and knotted or otherwise affixed together. These latter two approaches also may be employed to provide a secure connection between the pledget 52 and the withdrawal cord 58.

The withdrawal cord 58 is preferably non-absorbent along at least the location of its length. As used herein, the term "non-absorbent" refers to a structure formed predominantly of suitably hydrophobic materials such that upon contact with aqueous fluid such as menstrual fluid, it does not tend to attract, take in, wick or retain any substantial quantity of the fluid within its structure. In some examples it may be desired that the material(s) forming substantially the entire withdrawal cord 58 be hydrophobic, so that the withdrawal cord does not attract or wick menstrual fluid into or along its trailing portion, potentially out to its trailing end. The materials constituting the withdrawal cord may be inherently non-wettable or hydrophobic, or they may be treated to provide such properties. For example, a suitable wax may be applied to the material of the withdrawal cord 58 to decrease or eliminate wicking tendency. Other means for providing a material suitable for use as a withdrawal cord 58 which is non-absorbent and/or non-wicking are known in the art. For example, U.S. Pat. No. 5,458,589 describes one approach. However, the withdrawal cord 58 need not necessarily be non-wicking along its entire length, even if a non-absorbent withdrawal cord is desired. For example, it may be desirable to provide a withdrawal cord 58 in which at least a portion of the cord has a tendency or capability to wick deposited fluid upwardly toward the rearward end 17 of the pledget and into the structure thereof.

The withdrawal cord 58 need not have uniform properties throughout its length. For example, the portion of the withdrawal cord attached to or nearest the pledget 52 may be manufactured and/or treated so as to have wicking capability, while the free portion of the withdrawal cord 58 may be manufactured and/or treated so as to not have wicking capability. Other properties such as hydrophilicity/hydrophobicity, density, capillary size, width, thickness, and the like may also vary along the length of the withdrawal cord 58.

The withdrawal cord 58 may be formed of a strand or strands of component yarn or thread material. In some examples the yarn or thread material may be formed of cotton fiber, cotton fiber processed or treated to be suitably hydrophobic, other natural plant-based fiber which may be processed or treated to be suitably hydrophobic, or polyester, or a combination or blend thereof.

The component yarn or thread may be knitted, twisted or braided to form the withdrawal cord stock. For maximized tensile strength per unit decitex of the withdrawal cord stock, it may be desired that the component yarn or thread be of twisted or braided construction (rather than of knitted, woven or other construction).

Tampons of the type and configurations contemplated herein may also have or include any combination of features described in US 2020/0188189 and/or US 2020/0188190. Tampons of the type and configuration(s) contemplated herein may be manufactured via the processes described in those applications.

Relative Sliding Resistance Coefficient (CSR) Measurement Method

This method measures the static and kinetic resistance to relative sliding between two pairs of similar tampon applicator components, arranged crosswise to each other.

Although surface properties reflected in the measurement relate to friction and coefficients of friction, the term "sliding resistance" is employed herein because "friction" is not being measured via a conventional method. Friction is typically measured between objects with flat surfaces, which is not applicable in the present circumstances. The objects that are the subject of the measurement herein, however, typically do not have flat surfaces (they are typically cylindrical in shape). Any attempt to flatten the subject objects for a conventional friction measurement could substantially alter their surface features and also, possibly cause coatings to separate from the substrate, fracture or flake, causing unpredictable results that do not reflect the actual relevant conditions that the present method seeks to approximate.

The Relative Sliding Resistance Coefficient (CSR) between barrel or ejection plunger portions of tampon applicators is measured for purposes herein using a horizontally oriented constant rate of extension tester with a computer interface using an S-beam type load cell, with moment or off-axis side load cancelling capabilities, for which the forces measured are within 1% and 99% of the limit of the cell. A suitable instrument is a horizontally oriented MTS Criterion 42 interfaced with a computer running Testsuite software, as available from MTS Systems Corp., Eden Prairie, MN, or equivalent. All testing is performed in a conditioned room maintained at about 23° C.±2 C and about 50%±2% relative humidity.

The mounting fixtures and the overall test setup are schematically depicted in FIGS. 8A-8C and 9. Samples used in the test are all similar tampon applicator components, either ejection plungers, or barrel portions, of interest. A first pair of test samples 12 are held by an upper fixture 500U and pulled by the moveable crosshead 520 across the surfaces of a second pair of test samples 12 held by a lower fixture 500L that is affixed to a stationary portion 510 of the tensile tester. The upper fixture 500U is connected to the moveable crosshead 520 by a crosshead connection 515. The crosshead connection 515 is designed and constructed in any suitable way that ensures that the upper fixture 500U is pulled in a level linear direction horizontally and vertically aligned with the direction of movement of its point of attachment to the crossbeam of the tensile tester, and sideways motion of the upper fixture 500U relative the pulling direction and lower fixture 500L is prevented. The upper and lower fixtures, 500U and 500L, are identical to each other. They are formed of a lightweight material such as aluminum and have an overall size of about 43 mm wide by length L equal to the length of the test samples of interest. Each fixture has two parallel, identical grooves milled out or otherwise formed therein, that conform to the size and shape of the test samples. The two grooves are positioned at the center of each fixture directly adjacent to one another, with a spacing that is no more than 1 mm apart. The grooves run the entire length L of each fixture. The size of the grooves will be unique for the size of the samples being tested, and is based on the outer diameter thereof. The groove depth, GD, is 0.75×the outer diameter of the test samples of interest. The deepest portion of each groove has radius r, which is ½ the outer diameter of the test samples. A suitable weighting object (not shown) is selected and affixed in any suitable manner as necessary to rest securely in place on upper fixture 500U, to apply a total normal force N during the test of 560 g-f±1 g (equal to the weight of the upper fixture 500U plus that of the added weighting object).

Samples of tampons with applicators of interest are conditioned at 23° C.±3° C. and 50%±2% relative humidity two hours prior to testing. While handling test samples that have been removed from their primary wrappers, gloves (nitrile, or equivalent) must be worn to prevent transfer of oils or other contaminants, from the hands to the surfaces of the test samples. To execute a single replicate, four test samples 12 are required. The test samples are the hollow barrel portions, or alternatively, ejection plungers, of the subject tampon applicators. To prepare the test samples, remove the primary wrappers from four sample tampons. Using care to prevent any distortion to the shapes of the hollow components of interest, remove the ejection plunger by pulling it out of the barrel portion from its rearward end. Now remove the pledget from the rearward end of the barrel portion using the withdrawal cord. Discard the pledget and other components not being tested. Inspect the outer surfaces of the test samples to identify the test locations. The test location for each sample 12 is a smooth region (i.e. devoid of macroscopic surface features) that lies between the forward end and petals (if present) and any gripping surface features that may be present. The test location must have a substantially uniform outer diameter (OD). Now measure the OD of the samples at their test locations so that the correct size upper and lower fixtures can be prepared as previously described.

Place the test samples into the sized upper and lower test fixtures, 500U and 500L, as follows. Double-sided tape (no wider than ⅛ inch, no thicker than 5 mil; obtained from any convenient source) is used to secure the test samples in the fixtures to prevent sliding or rolling. Cut a strip of the tape to a length that is equal to length L and apply it centered at the deepest portion of one of the grooves in the upper fixture 500U. Remove the tape backing and then place one of the test samples into the groove on the tape, ensuring that the test sample is longitudinally centered within the groove. In like fashion, repeat the process for the adjacent groove in the upper fixture 500U, ensuring that the test samples are identically positioned in the fixture, with the forward end portions facing the same direction. Repeat for the lower fixture 500L with the remaining two test samples.

Affix the lower fixture 500L to a stationary portion 510 of the tensile tester (including any suitable elevating/adjustable stationary extension thereof) as follows. The longitudinal axes of the test samples in the lower fixture 500L are arranged to be parallel to the direction of motion of the crossbeam of the tensile tester, and the test samples must be level with each other. The height of the fixture is adjusted such that it allows the crosshead connection 515 to pull the upper fixture 500U along a horizontal/level direction when connected to the moveable crosshead 520 of the tensile tester and the upper fixture 500U. The width of the lower fixture 500L is centered with respect to the direction and location of pull on the upper fixture 500U.

Attach the upper fixture 500U to the moveable crosshead 520 of the tensile tester as follows. The fixture is attached such that the longitudinal axes of the test samples in the upper fixture 500U are perpendicular to the direction of motion of the crossbeam of the tensile tester as well as to the longitudinal axes of the lower test samples. Position the upper fixture 500U above the test samples in the lower fixture 500L so that when pulled across the lower test samples, there is at least 30 mm of travel distance between the upper and lower test samples along the test locations. Now attach the crosshead connection 515 to the upper fixture 500U and adjust the vertical positioning of the lower fixture 500L such that the crosshead connection 515 pulls the upper fixture 500U along a level direction when attached to the moveable crosshead 520. Now adjust the position of the moveable crosshead 520 such that the crosshead connection 515 is taut, with less than 1.0 g-f on the load cell. Zero the crosshead and place the weighting object on the top of the upper fixture 500U.

Program the tensile tester to move the crosshead away from the stationary fixture 500L at 4 mm/second for a distance of 30 mm. Force (g-f) and displacement (mm) data is recorded at 50 Hz.

Construct a graph of force versus displacement and record the peak force between 0 and 2 mm to the nearest 0.001 g-f, then divide by 560 g-f (normal force) and record as static CSR to the nearest 0.001 unitless digits. Calculate the average of all force peaks between 2 mm and 30 mm (the end of the test) to the nearest 0.001 g-f, then divide by 560 g-f (normal force) and record as kinetic CSR to the nearest 0.001 unitless digits. In like fashion, repeat the test for five replicate sets of like samples. Calculate the arithmetic mean for static CSR across all replicates and report as Relative Sliding Resistance Static CSR to the nearest 0.001. Calculate the arithmetic mean for kinetic CSR across all replicates and report as Relative Sliding Resistance Kinetic CSR to the nearest 0.001.

Gripping Slip Resistance (CGSR) Measurement Method

This method measures the static and kinetic resistance to relative slip between a surface of a sheet of skin mimic material and a pair of similar tampon applicator components. It is intended to approximate resistance to relative slipping between human skin (as on a finger) and the surface of the material of the applicator components.

Although surface properties reflected in the measurement relate to friction and coefficients of friction, the term "gripping slip resistance" is employed herein because "friction" is not being measured via a conventional method. Friction is typically measured between objects with flat surfaces, which is not applicable in the present circumstances. The objects that are the subject of the measurement herein, however, typically do not have flat surfaces (they are typically cylindrical in shape). Any attempt to flatten the subject objects for a conventional friction measurement could substantially alter their surface features and also, possibly cause coatings to separate from the substrate, fracture or flake, causing unpredictable results that do not reflect the actual relevant conditions that the present method seeks to approximate.

The Gripping Slip Resistance Coefficient (CGSR) between a skin mimic material and the barrel or ejection plunger portions of tampon applicators is measured for purposes herein using a horizontally oriented constant rate of extension tester with a computer interface using an S-beam type load cell, with moment or off-axis side load cancelling capabilities, for which the forces measured are within 1% and 99% of the limit of the cell. A suitable instrument is a horizontally oriented MTS Criterion 42 interfaced with a computer running Testsuite software, as available from MTS Systems Corp., Eden Prairie, MN, or equivalent. All testing is performed in a conditioned room maintained at about 23° C.±2 C and about 50%±2% relative humidity.

The mounting fixtures and the overall test setup are schematically depicted in FIGS. 8A-8C and 10. Samples used in the test are all similar tampon applicator components, either ejection plungers, or barrel portions, of interest. A first pair of test samples 12 are held by an upper fixture 500U and pulled by the moveable crosshead 520 across the surface of a sheet of skin mimic material 512 affixed to and supported by a stationary portion 510 of the tensile tester. The upper fixture 500U is connected to the moveable crosshead 520 by a crosshead connection 515. The crosshead connection 515 is designed and constructed in any suitable way that ensures that the upper fixture 500U is pulled in a level linear direction horizontally and vertically aligned with the direction of movement of its point of attachment to the crossbeam of the tensile tester, and sideways motion of the upper fixture 500U relative the pulling direction and the affixed skin mimic is prevented. The upper fixture is formed of a lightweight material such as aluminum and has an overall size of about 43 mm wide by length L equal to the length of the test samples of interest. The fixture has two parallel, identical grooves milled out or otherwise formed therein, that conform to the size and shape of the test samples. The two grooves are positioned at the center of the fixture directly adjacent to one another, with a spacing that is no more than 1 mm apart. The grooves run the entire length L of the fixture. The size of the grooves will be unique for the size of the samples being tested, and is based on the outer diameter thereof. The groove depth, GD, is 0.75×the outer diameter of the test samples of interest. The deepest portion of each groove has radius r, which is ½ the outer diameter of the test samples. A suitable weighting object (not shown) is selected and affixed in any suitable manner as necessary to rest securely in place on upper fixture 500U, to apply a total normal force N during the test of 560 g-f±1 g (equal to the weight of the upper fixture 500U plus that of the added weighting object).

The skin mimic material, for purposes herein, is a sheet of dry collagen material. A suitable collagen material is Naturin Coffi collagen sheets (available from Viscofan USA Inc., 50 Country Court, Montgomery, AL 36105, USA), or equivalent. The collagen material sheet is cut into pieces that are wider than the length of the test samples, and about 100 mm long. A fresh cut sheet of the collagen material is used for each test replicate and must be obtained from a smooth, uniform section of the larger sheets (i.e. devoid of any wrinkles or other surface defects).

Samples of tampons with applicators of interest and the collagen skin mimic are conditioned at 23° C.±3° C. and 50%±2% relative humidity two hours prior to testing. While handling the collagen and test samples that have been removed from their primary wrappers, gloves (nitrile, or equivalent) must be worn to prevent transfer of oils or other contaminants, from the hands to the surfaces of the collagen and test samples. To execute a single replicate, two test samples 12 are required. The test samples are the hollow barrel portions, or alternatively, ejection plungers, of the subject tampon applicators. To prepare the test samples, remove the primary wrappers from two sample tampons. Using care to prevent any distortion to the shapes of the hollow components of interest, remove the ejection plunger by pulling it out of the barrel portion from its rearward end. Now remove the pledget from the rearward end of the barrel portion using the withdrawal cord. Discard the pledget and other components not being tested. Inspect the outer surfaces of the test samples to identify the test locations. The test location for each sample 12 is a smooth region (i.e. devoid of macroscopic surface features) that lies between the forward end and petals (if present) and any gripping surface features that may be present. Only a portion of the sample having a section of continuous cylindrical surface with no discontinuities, that may be placed in contact with the skin mimic material and pulled thereacross, should be tested. If a portion of the sample of interest such as a barrel portion bears formed macroscopic gripping surface features or other impressed, embossed or otherwise formed macroscopic features that create discontinuities in the cylindrical surface of the sample, carefully cut the featured portion away from the sample along a direction perpendicular to its longitudinal axis, using a thin sharp blade (such as an X-ACTO brand knife with a fresh blade, Newell Brands, Atlanta, Georgia) or other suitable cutting implement so as to enable cutting without causing permanent deformation of the cylindrical shape of the remainder of the sample. The test location must have a substantially uniform outer diameter (OD). Now measure the OD of the samples at their test locations so that the correct size barrel fixtures can be prepared as previously described.

Place the test samples into the sized upper barrel test fixture, 500U, as follows. Double-sided tape (no wider than ⅛ inch, no thicker than 5 mil; obtained from any convenient source) is used to secure the test samples in the fixture to prevent sliding or rolling. Cut a strip of the tape to a length that is equal to length L and apply it centered at the deepest portion of one of the grooves in the upper fixture 500U. Remove the tape backing and then place one of the test samples into the groove on the tape, ensuring that the test sample is longitudinally centered within the groove. In like fashion, repeat the process for the adjacent groove in the upper fixture 500U, ensuring that the test samples are identically positioned in the fixture, with the forward end portions facing the same direction.

Affix a single cut sheet of the skin mimic material 512 to a stationary portion 510 of the tensile tester (including any suitable elevating/adjustable stationary extension thereof) as follows. The stationary portion 510 must have a flat, level, smooth, rigid surface. The height of the stationary portion 510 is adjusted such that it allows the crosshead connection 515 to pull the upper fixture 500U along a horizontal/level direction when connected to the moveable crosshead 520 of the tensile tester and the upper fixture 500U. The width of the stationary portion 510 is centered with respect to the direction and location of pull on the upper fixture 500U. The cut skin mimic material sheet 512 is laid flat with its short axis centered under the upper fixture 500U and its long axis parallel to the pull direction of the moveable crosshead 520. A strip of masking tape (1" wide; obtained from any convenient source) is used to secure the collagen piece 512 to the stationary portion 510. The strip of tape is placed across the end of the collagen that is furthest away from the moveable crosshead 520 in such a way that the tape overlaps about 10 mm of the collagen piece and extends across its entire width.

Attach the upper fixture 500U to the moveable crosshead 520 of the tensile tester as follows. The fixture is attached such that the longitudinal axes of the test samples in the upper fixture 500U are perpendicular to the direction of motion of the crossbeam of the tensile tester. Position the upper fixture 500U above the affixed collagen piece 512 so that when pulled across the collagen, there is at least 50 mm of travel distance between the upper test samples along the collagen in a region devoid of the strip of tape. Now attach the crosshead connection 515 to the upper fixture 500U and adjust the vertical positioning of the surface of the stationary portion 510 with affixed collagen 512 such that the crosshead connection 515 pulls the upper fixture 500U along a level direction when attached to the moveable crosshead 520. Now adjust the position of the moveable crosshead 520 such that the crosshead connection 515 is taut, with less than 1.0 g-f on the load cell. Zero the crosshead and place the weighting object on the top of the upper fixture 500U.

Program the tensile tester to move the crosshead away from the stationary fixture 510 at 4 mm/second for a distance of 50 mm. Force (g-f) and displacement (mm) data is recorded at 50 Hz.

Construct a graph of force versus displacement and record the peak force between 0 and 2 mm to the nearest 0.001 g-f, then divide by 560 g-f (normal force) and record as static CGSR to the nearest 0.001 unitless digits. Calculate the average of all force peaks between 2 mm and 50 mm (the end of the test) to the nearest 0.001 g-f, then divide by 560 g-f (normal force) and record as kinetic CGSR to the nearest 0.001 unitless digits. In like fashion, repeat the test for five replicate sets of like samples. Calculate the arithmetic mean for static CGSR across all replicates and report as Relative Gripping Slip Resistance Static CGSR to the nearest 0.001. Calculate the arithmetic mean for kinetic CGSR across all replicates and report as Relative Gripping Slip Resistance Kinetic CGSR to the nearest 0.001.

In view of the foregoing disclosure, the following examples are contemplated herein:

1. A tampon product comprising a tampon, the tampon comprising a pledget (52) with an attached withdrawal cord (58), the tampon being housed within an applicator (10), the applicator comprising a hollow barrel portion (12) and an ejection plunger (30) arranged within the barrel portion and longitudinally slidable therewithin, at least one of the barrel portion and the ejection plunger having a cylindrical form and comprising a paper, and having an outer surface formed by a coating (103) applied directly over the paper and not predominately constituted by a material derived from petroleum, the at least one of the barrel portion and the ejection plunger exhibiting a static CSR no greater than 0.250, preferably no greater than 0.230, and more preferably no greater than 0.210; and preferably, the at least one of the barrel portion and the ejection plunger exhibiting a kinetic CSR no greater than 0.210, preferably no greater than 0.190, and more preferably no greater than 0.175.

2. A tampon product comprising a tampon, the tampon comprising a pledget (52) with an attached withdrawal cord (58), the tampon being housed within an applicator (10), the applicator comprising a hollow barrel portion (12) and an ejection plunger (30) arranged within the barrel portion and longitudinally slidable therewithin, at least one of the barrel portion and the ejection plunger having a cylindrical form and comprising a paper, and having an outer surface formed by a coating (103) applied directly over the paper and not predominately constituted by a material derived from petroleum, the at least one of the barrel portion and the ejection plunger exhibiting a static CSR no less than 0.190, more preferably no less than 0.200, and even more preferably no less than 0.210; and preferably, the at least one of the barrel portion and the ejection plunger exhibiting a kinetic CSR no less than 0.170, more preferably no less than 0.180, and even more preferably no less than 0.190.

3. The tampon product of example 1, the at least one of the barrel portion and the ejection plunger exhibiting a static CGSR no less than 0.190, more preferably no less than 0.200, and even more preferably no less than 0.210; and preferably the at least one of the barrel portion and the ejection plunger exhibiting a kinetic CGSR no less than 0.170, more preferably no less than 0.180, and even more preferably no less than 0.190.
4. The tampon product of any of the preceding examples wherein the coating (103) comprises a natural wax.
5. The tampon product of example 4 wherein the coating is predominantly constituted by the natural wax.
6. The tampon product of either of examples 4 or 5 wherein the natural wax is a vegetable wax.
7. The tampon product of example 6 wherein the vegetable wax is selected from the group consisting of bayberry wax, candelilla wax, carnauba wax, castor wax, esparto wax, Japan wax, jojoba wax, ouricury wax, rice bran wax, soy wax, sunflower wax, tallow tree wax, and combinations thereof.
8. The tampon product of either of examples 4 or 5 wherein the wax is selected from the group consisting of candelilla wax, sunflower wax, shellac wax, rice bran wax, castor wax and carnauba wax, and combinations thereof.
9. The tampon product of any of the preceding examples wherein each of the barrel portion (12) and the ejection plunger (30) has an outer layer comprising a substrate paper (100b) bearing the coating.
10. The tampon product of any of the preceding examples wherein the at least one of the barrel portion (12) and the ejection plunger (30) comprises a plurality of layers of spiral wound paper, the layers of the plurality being affixed together by a glue applied therebetween.
11. The tampon product of example 10 wherein the glue is not predominantly constituted by a material derived from petroleum.
12. The tampon product of either of examples 10 or 11 wherein the glue comprises starch.
13. The tampon product of example 12 wherein the glue in a substantially dry state is predominantly constituted by starch.
14. The tampon product of either of examples 12 or 13 wherein the glue comprises sodium aluminate.
15. The tampon product of any of the preceding claims, wherein the hollow barrel portion (12) and the ejection plunger (30) are substantially or entirely free of any material derived from petroleum.
16. A method for manufacturing tampon products of any of the preceding examples, comprising the step of conveying or translating pluralities of tampon applicator components comprising one or more of barrel portions (12), ejection plungers (30) or cut lengths of tube stock constituting precursors thereof, along a machine direction (MD), wherein during such conveying or translating, longitudinal axes of the components in the pluralities are substantially aligned with a cross direction (CD), wherein outer surfaces of components in the pluralities contact each other.
17. The method of example 16 wherein components in the pluralities roll along the machine direction in sequence, and their respective outer surfaces in contact slide against each other.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tampon product comprising a tampon, the tampon comprising a pledget with an attached withdrawal cord, the tampon being housed within an applicator, the applicator comprising a hollow barrel portion and an ejection plunger arranged within the barrel portion and longitudinally slidable therewithin, at least one of the barrel portion and the ejection plunger having a cylindrical form and comprising a paper, and having an outer surface formed by a coating applied directly over a surface texture of the paper imparted by one selected from the group consisting of compressing felt, screen mesh, surface textures of calendar rollers, creping, and combinations thereof, wherein the coating comprises a natural wax, and wherein the at least one of the barrel portion and the ejection plunger exhibiting a static Relative Sliding Resistance Coefficient no greater than 0.250; and the at least one of the barrel portion and the ejection plunger exhibiting a kinetic Relative Sliding Resistance Coefficient no greater than 0.210.

2. A tampon product comprising a tampon, the tampon comprising a pledget with an attached withdrawal cord, the tampon being housed within an applicator, the applicator comprising a hollow barrel portion and an ejection plunger arranged within the barrel portion and longitudinally slidable therewithin, at least one of the barrel portion and the ejection plunger having a cylindrical form and comprising a paper, and having an outer surface formed by a coating applied directly over a surface texture of the paper, the surface texture comprising a plurality of ridges approximating a crystal structure of paraffin wax, wherein the surface texture is imparted by one selected from the group consisting of compressing felt, screen mesh, surface textures of calendar rollers, creping, and combinations thereof, wherein the coating comprises a natural wax, and wherein the at least one of the barrel portion and the ejection plunger exhibiting a static Gripping Slip Resistance Coefficient no less than 0.190; and a kinetic Gripping Slip Resistance Coefficient no less than 0.170, and wherein the at least one of the barrel portion and the ejection plunger exhibiting a static Relative Sliding Resistance Coefficient no greater than 0.250; and the at least one of the barrel portion and the ejection plunger exhibiting a kinetic Relative Sliding Resistance Coefficient no greater than 0.210.

3. The tampon product of claim 1, the at least one of the barrel portion and the ejection plunger exhibiting a static Gripping Slip Resistance Coefficient no less than 0.190; and a kinetic Gripping Slip Resistance Coefficient no less than 0.170.

4. The tampon product of claim 1 wherein the coating is predominantly constituted by the natural wax.

5. The tampon product of claim 4 wherein the natural wax is a vegetable wax.

6. The tampon product of claim 5 wherein the vegetable wax is selected from the group consisting of bayberry wax, candelilla wax, carnauba wax, castor wax, esparto wax, Japan wax, jojoba wax, ouricury wax, rice bran wax, soy wax, sunflower wax, tallow tree wax, and combinations thereof.

7. The tampon product of claim 4 wherein the wax is selected from the group consisting of candelilla wax, sunflower wax, shellac wax, rice bran wax, castor wax and carnauba wax, and combinations thereof.

8. The tampon product of claim 1 wherein each of the barrel portion and the ejection plunger has an outer layer comprising a substrate paper bearing the coating.

9. The tampon product of claim 1 wherein the at least one of the barrel portion and the ejection plunger comprises a plurality of layers of spiral wound paper, the layers of the plurality being affixed together by a glue applied therebetween.

10. The tampon product of claim 9 wherein the glue is not predominantly constituted by a material derived from petroleum.

11. The tampon product of claim 10 wherein the glue comprises starch.

12. The tampon product of claim 11 wherein the glue in a substantially dry state is predominantly constituted by starch.

13. The tampon product of claim 12 wherein the glue comprises sodium aluminate.

14. The tampon product of claim 2 wherein the coating is predominately constituted by a vegetable wax.

15. The tampon product of claim 14 wherein the wax is selected from the group consisting of candelilla wax, sunflower wax, shellac wax, rice bran wax, castor wax and carnauba wax, and combinations thereof.

16. The tampon product of claim 2 wherein each of the barrel portion and the ejection plunger has an outer layer comprising a substrate paper bearing the coating.

17. The tampon product of claim 2 wherein the at least one of the barrel portion and the ejection plunger comprises a plurality of layers of spiral wound paper, the layers of the plurality being affixed together by a glue applied therebetween.

18. The tampon product of claim 17 wherein the glue in a substantially dry state is predominantly constituted by starch, and comprises sodium aluminate.

19. A method for manufacturing tampon products of claim 1, comprising the step of conveying or translating pluralities of tampon applicator components comprising one or more of barrel portions, ejection plungers or cut lengths of tube stock constituting precursors thereof, along a machine direction (MD), wherein during such conveying or translating, longitudinal axes of the components in the pluralities are substantially aligned with a cross direction (CD), wherein outer surfaces of components in the pluralities contact each other.

* * * * *